US009063151B2

(12) United States Patent
Parussini et al.

(10) Patent No.: US 9,063,151 B2
(45) Date of Patent: Jun. 23, 2015

(54) METHODS FOR DETECTING ANTIBODIES

(75) Inventors: Ermis Parussini, Lentilly (FR); Guillaume Noguier, Bussy Saint George (FR)

(73) Assignee: THERADIAG SA, Croissy-Beaubourg (FR)

(*) Notice: Subject to any disclaimer, the term of this patent is extended or adjusted under 35 U.S.C. 154(b) by 29 days.

(21) Appl. No.: 13/642,874

(22) PCT Filed: Apr. 28, 2011

(86) PCT No.: PCT/EP2011/056732
§ 371 (c)(1),
(2), (4) Date: Dec. 14, 2012

(87) PCT Pub. No.: WO2011/135024
PCT Pub. Date: Nov. 3, 2011

(65) Prior Publication Data
US 2013/0108631 A1 May 2, 2013

Related U.S. Application Data

(60) Provisional application No. 61/329,201, filed on Apr. 29, 2010.

(30) Foreign Application Priority Data

Apr. 29, 2010 (EP) .................................... 10305455

(51) Int. Cl.
*G01N 33/68* (2006.01)
*G01N 33/564* (2006.01)
*G01N 33/94* (2006.01)

(52) U.S. Cl.
CPC .......... *G01N 33/6854* (2013.01); *G01N 33/564* (2013.01); *G01N 33/9493* (2013.01); *G01N 2333/525* (2013.01); *G01N 2800/52* (2013.01)

(58) Field of Classification Search
None
See application file for complete search history.

(56) References Cited

FOREIGN PATENT DOCUMENTS

WO  WO 2008/125903  10/2008
WO  WO 2009 117791  10/2009

OTHER PUBLICATIONS

Shankar et al. Recommendations for the validation of immunoassays used for detection of host antibodies against biotechnology products. J Pharm Biomed Anal. Dec. 15, 2008;48(5):1267-81. Epub Sep. 19, 2008.*
Patton, A. et al. "An acid dissociation bridging ELISA for detection of antibodies directed against therapeutic proteins in the presence of antigen" *Journal of Immunological Methods*, Sep. 1, 2005, pp. 189-195, vol. 304.
Wolbink, G. J. et al. "Development of Antiinfliximab Antibodies and Relationship to Clinical Response in Patients with Rheumatoid Arthritis" *Arthritis & Rheumatism*, Mar. 1, 2006, pp. 711-715, vol. 54, No. 3.
Written Opinion in International Application No. PCT/EP2011/056732, Jul. 1, 2011, pp. 1-6.

* cited by examiner

*Primary Examiner* — David Romeo
(74) *Attorney, Agent, or Firm* — Saliwanchik, Lloyd & Eisenschenk

(57) ABSTRACT

The present invention relates to methods of detecting Anti-Drug Antibodies. The present invention also relates to methods of monitoring patients undergoing therapeutic antibody treatment. The invention further relates to kits suitable for the implementation of the above methods.

9 Claims, 3 Drawing Sheets

METHODS FOR DETECTING ANTIBODIES

CROSS-REFERENCE TO RELATED APPLICATIONS

Figure 1:
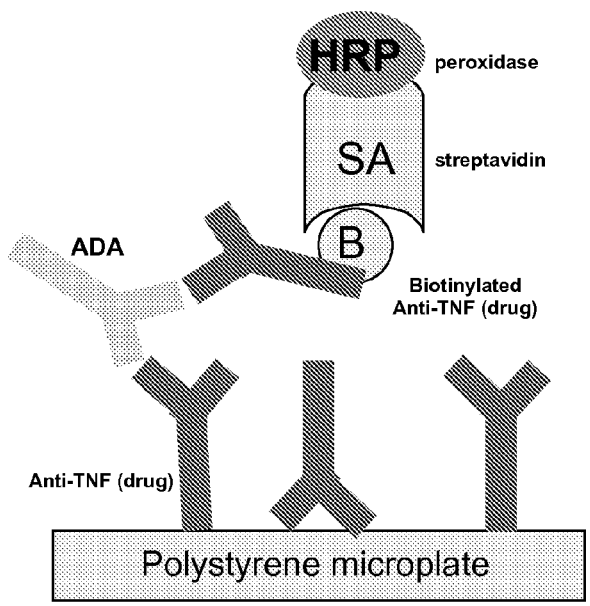

This application is the U.S. national stage application of International Patent Application No. PCT/EP2011/056732, filed Apr. 28, 2011, which claims the benefit of U.S. Provisional Patent Application No. 61/329,201, filed Apr. 29, 2010, the disclosures of which are hereby incorporated by reference in their entireties, including all figures, tables and amino acid or nucleic acid sequences.

The present invention relates to methods of detecting Anti-Drug Antibodies. The present invention also relates to methods of monitoring patients undergoing therapeutic antibody treatment. The invention further relates to kits suitable for the implementation of the above methods.

BACKGROUND

Therapeutic antibodies are increasingly being used for the treatment of various disorders, such as immunological disorders, inflammatory disorders, cancers or infectious diseases. These therapeutic antibodies are typically monoclonal antibodies, derived from various species, or chimeric or humanized antibodies (see e.g., Levene et al., 2005, J. Royal Soc. Med. 98, pp 145-152). Depending on the disease, therapeutic antibodies directed against the following distinct target antigens have been used: TNFα, VEGF, HER2, CD20, IGF-I receptor, EGFR, or the IL-6 receptor, for instance.

Anti-TNFα therapeutic antibodies are widely used to treat patients with various inflammatory or autoimmune diseases, including rheumatoid arthritis, multiple sclerosis, Crohn's disease or ankylosing spondylitis. Examples of such anti-TNFα agents include Etanercept, Golimumab, Certolizumab pegol, Adalimumab, or Infliximab. Etanercept is a dimeric fusion protein consisting of two extracellular domains of the human p75 TNFα receptor, linked to the Fc fragment of a type 1 human immunoglobulin (IgG1). Golimumab is a human anti-TNFα monoclonal antibody. Certolizumab pegol is a monoclonal antibody, more precisely a PEGylated Fab' fragment of a humanized anti-TNFα monoclonal antibody. Adalimumab is a humanized anti-TNFα monoclonal antibody and Infliximab is a chimeric anti-TNFα monoclonal antibody (Perdriger A, Infliximab in the treatment of rheumatoid arthritis. Biologics: Targets & Therapy 2009:3 183-191). These antibodies bind TNFα and block its inflammatory action.

Further examples of therapeutic antibodies include, without limitation, an anti-IL-6R monoclonal antibody as disclosed in WO2004/096274 and an anti-IGF-IR antibody as disclosed for instance in WO2005/005635.

During treatment with therapeutic antibodies, however, an immune response against the therapeutic antibody itself can be raised, and patients often develop, over the course of the treatment, antibodies against the drug itself ("Anti-Drug Antibodies"). As a result, the plasmatic rate of therapeutic antibody decreases and simultaneously or subsequently, the disease symptoms reappear or increase. These Anti-Drug Antibodies ("ADA") therefore reduce or totally neutralize the effect of a therapeutic antibody (see e.g., Wolbink G J, et al. Development of anti-Infliximab antibodies and relationship to clinical response in patients with rheumatoid arthritis. Arthritis & Rheumatism, 2006 54(3): 711-715; G. M. Bartelds, et al. High levels of human antibodies to adalimumab in a patient not responding to adalimumab treatment. Anna Rheum Dis 2006; 65:1249-1250). The detection of these ADA in samples from a subject therefore may represent a method of monitoring patients over the course of the treatment.

Methods for detecting ADA have been reported in the art, such as for instance in WO2008/137885, WO2007/101661, or WO2009/091240. The methods referred to in these applications are immunological methods using capture and label antibodies. Further methods and recommendations regarding ADA detection have been reported in Anthony R. Mire-Sluis, et al., Journal of Immunological Methods, 333 (2008) 1-9; Eugen Koren, et al., Journal of Immunological Methods, 289 (2004) 1-16. Wolbink et al (Arthritis & Rheumatism 54 (2006) 711-715) also discusses the clinical relevance of anti-infliximab antibodies in patients with rheumatoid arthritis. None of these methods propose to simultaneously evaluate ADA and the relevant antigen. None of these methods recognize the relevance of a combined detection of various parameters.

Patton et al (J. Immunol. Methods 304 (2005) 189-195) relates to an ELISA method for detecting antibodies against proteins.

The present invention relates to improved methods of detecting ADA and monitoring patients undergoing therapeutic antibody treatments.

SUMMARY OF THE INVENTION

The present invention provides improved immunological methods of detecting Anti-Drug Antibodies. The present invention also provides methods of monitoring patients undergoing therapeutic antibody treatment. The invention further relates to kits suitable for the implementation of the above methods.

More specifically, an object of the present invention relates to a method for immuno-detecting (the presence or amount of) an Anti-Drug Antibody (ADA) in a sample (in vitro), wherein the Drug is a therapeutic antibody directed against a target antigen, the method comprising:
  a) verifying the presence of the antigen in the sample;
  b) if present, neutralizing the antigen in the sample; and
  c) immuno-detecting (the presence or amount of) said ADA in said sample.

The inventors have discovered that the presence of the antigen in the sample substantially hampers the ability to detect the corresponding ADA. Accordingly, absent such a prior neutralization step, no reliable detection of ADA in a sample can be obtained.

A further object of this invention is a method for immuno-detecting an Anti-Drug Antibody (ADA) in a sample (in vitro), wherein the Drug is a therapeutic antibody directed against a target antigen, the method comprising:
  a) treating the sample to neutralize the antigen that may be present; and
  b) immuno-detecting the presence or amount of said ADA in said sample.

The invention also relates to a method for detecting the responsiveness of a patient to a therapeutic antibody treatment, wherein the therapeutic antibody is directed against a target antigen, the method comprising determining, in a sample from the patient, the presence or amount of:
  the therapeutic antibody,
  the antigen, and
  Anti-Drug Antibodies directed against said therapeutic antibody; to obtain a patient profile, wherein the patient profile indicates the responsiveness to said treatment.

Preferably, in the above method, if the antigen is present in the sample, then a further step of determining the presence of said ADA is performed after treatment of the sample to neutralize the antigen. Accordingly, in a preferred embodiment, the invention relates to a method for detecting the responsiveness of a patient to a therapeutic antibody treatment, wherein the therapeutic antibody is directed against a target antigen, the method comprising:
(a) determining, in a sample from the patient, the presence or amount of:
the therapeutic antibody,
the antigen, and
Anti-Drug Antibodies directed against said therapeutic antibody;
(b) if the antigen is detected in the sample in step (a), then treating a further sample of the subject to neutralize the antigen and determining again the presence of said ADA in said treated sample, thereby obtaining a patient profile, wherein the patient profile indicates the responsiveness to said treatment.

Said method is preferably performed at different points of times over the course of the treatment of the patient, so that the responsiveness of the patient, or the efficacy of the treatment, can be monitored and, if appropriate, the treatment may be adjusted.

In a further embodiment, the invention also relates to a method for detecting the responsiveness of a patient to a therapeutic antibody treatment, wherein the therapeutic antibody is directed against TNFalpha, the method comprising determining, in a sample from the patient, the presence or amount of inactive TNFalpha, said presence or amount being indicative of low or decreasing responsiveness of the patient to said treatment. In a preferred embodiment, the method also comprises a determination of the presence or amount of the therapeutic antibody and Anti-Drug Antibodies directed against said therapeutic antibody to obtain a patient profile, wherein the patient profile indicates the responsiveness to said treatment.

The invention also relates to a method for treating a patient, the method comprising administering to the patient an effective amount of a therapeutic antibody directed against a target antigen and assessing the responsiveness of the patient to said therapeutic antibody treatment as disclosed above.

A further object of the invention relates to a kit comprising reagents to detect, in a sample, the presence or amount of
a therapeutic antibody directed against a target antigen,
the antigen, and
Anti-Drug Antibodies directed against said therapeutic antibody.

The method is preferably performed by ELISA or immuno-capture, and the antigen is preferably TNFα.

LEGEND TO THE FIGURES

Figure 2:
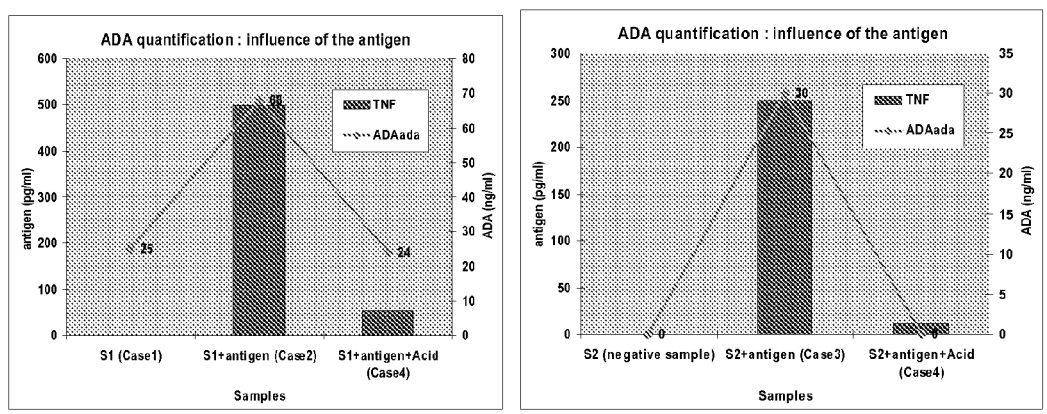
Figure 3:
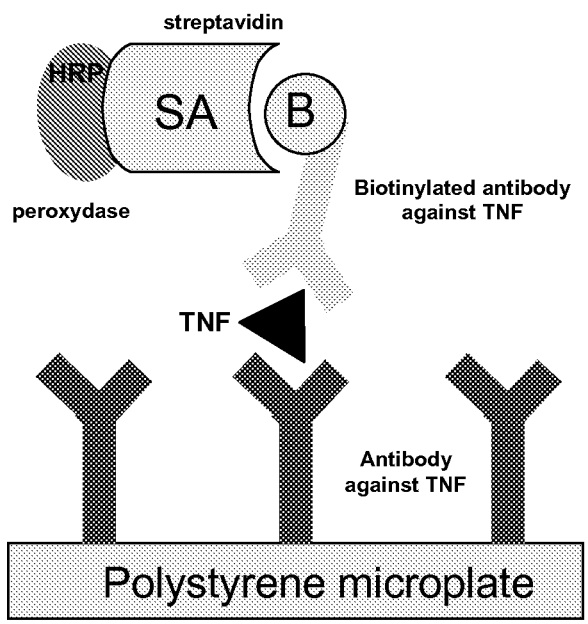
Figure 4:
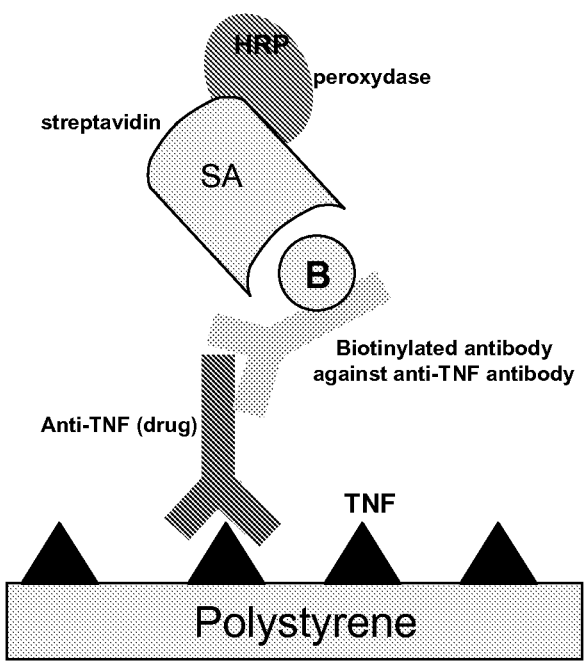
Figure 5:
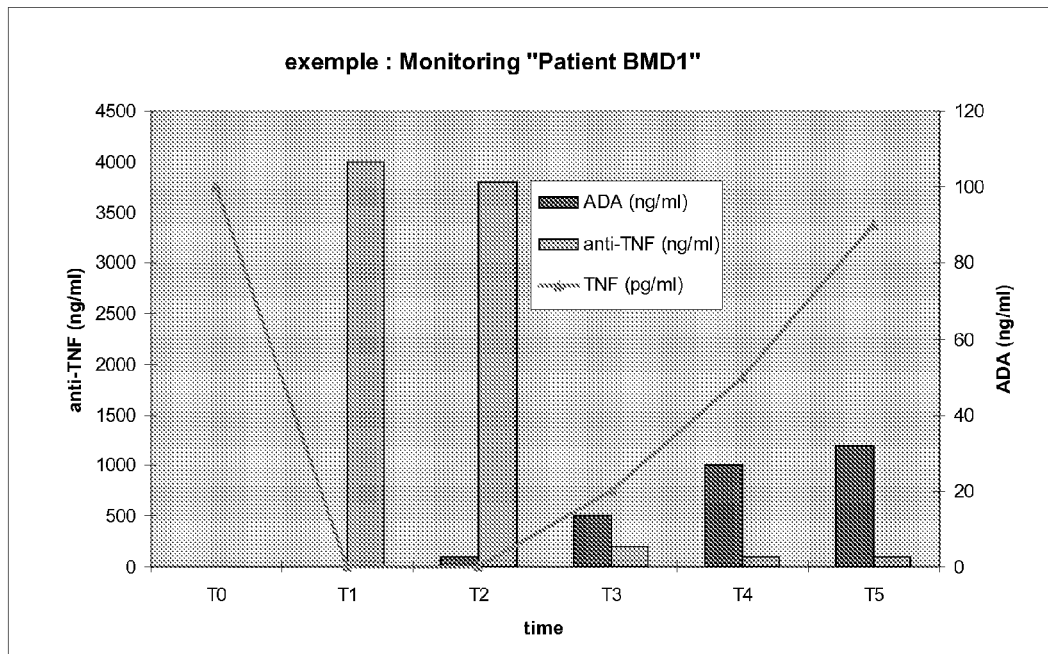
Figure 6:
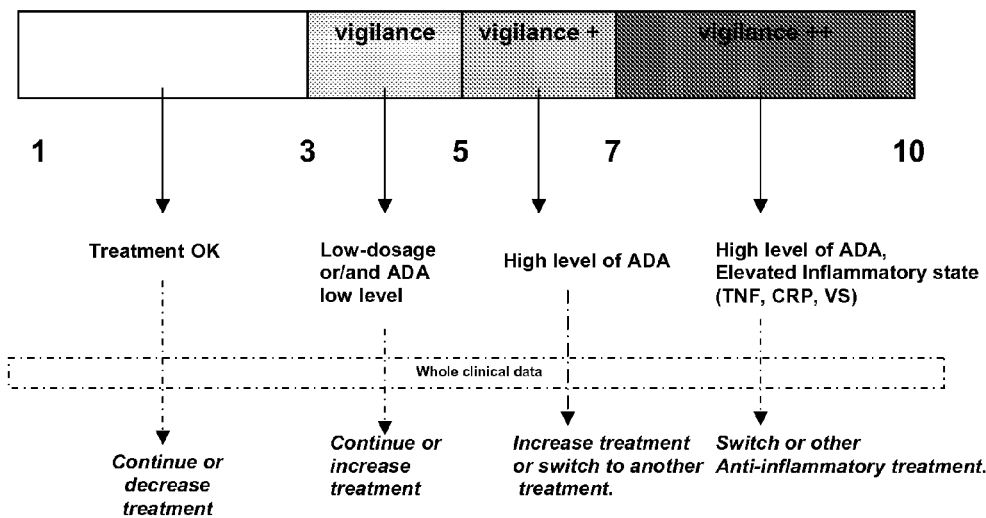

FIG. 1: ADA quantification. HRP: Horse Radish Peroxidase, SA: Streptavidin; B: Biotin.
FIG. 2: Influence of antigen on ADA determination.
FIG. 3: TNFα quantification.
FIG. 4: Anti-TNFα quantification.
FIG. 5: Patient monitoring
FIG. 6: Representative monitoring score values

DETAILED DESCRIPTION OF THE INVENTION

The invention relates to compositions, kits and methods for detecting ADAs and for monitoring patients undergoing therapeutic antibody treatment. The invention discloses improved ADA detection methods which provide reliable data and information. The inventors have shown that pretreating a sample to neutralize any antigen present in the sample is essential to make a reliable ADA assessment. The inventors have also demonstrated that the simultaneous determination, in a sample from the subject, of three parameters (ADA, antigen, Drug) provides a predictive profile of patient evolution and response to the treatment. The invention therefore provides an efficient method of monitoring patients undergoing therapeutic antibody treatment, and allows a proper and efficient adjustment of treatment regimen.

The invention will be best understood by reference to the following definitions:

DEFINITIONS

The term "therapeutic antibody" according to the invention denotes any antibody which can be administered to a subject as an active agent. Particular examples of such therapeutic antibodies are antibodies used in the treatment of inflammatory disorders, such as rheumatoid arthritis or osteoarthritis. These include, specifically, anti-TNFα antibodies. The term "therapeutic antibody" also includes antibody derivatives or antigen-specific ligand molecules, such as antibody Fab fragments, or antibody Fc fragments, synthetic receptors, soluble receptors, and the like, that selectively bind a target antigen.

The term "ADA" or "Anti-Drug-Antibody" designates an antibody which binds to a therapeutic antibody in a subject. ADA may bind various epitopes in a therapeutic antibody, including variable regions or constant regions.

As used therein, the term "subject" or "patient" designates any mammalian subject or patient, preferably a human subject or patient.

As used therein the term "combined" determination indicates that the specified markers are assessed in the sample, either simultaneously or sequentially. Concomitant assessment is not required, although preferred and more convenient.

The term "sample" indicates any sample susceptible to contain antibodies. This term preferably designates a biological fluid, such as serum, plasma or total blood, or a derivative thereof (e.g., resulting from dilution, pre-treatment, enrichment, lysis, etc. of a biological fluid). The sample is preferably a plasma, blood or serum sample or a dilution thereof.

ADA Determination

The present invention relates to improved methods for determining ADA in a sample. This aspect of the invention stems, inter alia, from the discovery that the antigen itself affects the quantitative determination of ADA in the sample. As shown in the experimental section, in the presence of the antigen in the tested sample, the measured amount of ADA are substantially overestimated, rendering the test useless and non reliable. The invention shows that, by first neutralizing the antigen in the sample, a reliable measure can be obtained. The invention thus relates to a method for immuno-detecting an Anti-Drug Antibody (ADA) in a sample (in vitro), wherein the Drug is a therapeutic antibody directed against a target antigen, the method comprising:
a) verifying the presence of the antigen in the sample;
b) if present, neutralizing the antigen in the sample; and
c) immuno-detecting the presence or amount of said ADA in said sample.

The invention also relates to a method for immuno-detecting an Anti-Drug Antibody (ADA) in a sample, wherein the Drug is a therapeutic antibody directed against a target antigen, the method comprising:
a) treating the sample to neutralize the antigen that may be present; and
b) immuno-detecting the presence or amount of said ADA in said sample.

The step of neutralizing the antigen can be performed by different techniques. Preferably, the antigen is neutralized by acid treatment of the sample (generally followed by neutralization of the acid), by depleting or capturing the antigen in the sample, or by immuno-neutralization.

For acid treatment, the sample is preferably treated to reduce the pH below 4, more preferably to a range comprised between about 2.5 and 3.5. This may be accomplished by adding to the sample, before the reaction, an acid solution under conditions (e.g., concentration and strength) suitable to reduce the pH to the above preferred range. Examples of suitable acids include carboxylic acids such as acetic acid, hydrochloric acid, or sulfuric acid. Preferably, after acid treatment, the pH of the sample is neutralized, at least partially, prior to detecting ADA. This neutralization may be obtained by adding a basic solution to the sample. Acid treatment thus typically comprises:

adding to the sample, before the reaction, an acid solution, to reduce the pH below about 4;

incubating the acidified sample at room temperature; and adding to the acidified sample, before reaction, a basic solution, such as TRIS buffer, or Phosphate buffer, or carbonate buffer, or borate buffer to neutralize the acid and restore a pH above 4, typically between 5 and 9, more typically between 6 and 8.

The antigen may also be neutralized by capture or depletion using any suitable affinity reagent. Typically, the sample is contacted with a support coated with or containing a binding reagent specific for the antigen. Upon passage or contacting, the antigen is immobilized or retained by the support, and the collected or resulting sample is substantially devoid of free antigen. The sample may be treated through a column coated with an antibody specific for the antigen. Alternatively, beads coated with such an antibody may be added to the sample and optionally subsequently separated or removed from the medium.

Immuno-neutralization may be carried out by monoclonal or polyclonal antibodies;

In a preferred embodiment, the antigen is neutralized by acid treatment

Immunodetection of ADA can be carried out by different types or platforms of immuno-assays including, without limitation, ELISA, immunocapture, microarrays (protein chips), Flow cytometry (including e.g., Fidis), or multiplex dot.

In preferred embodiments, ADA is immunodetected by ELISA or immunocapture. In such methods, a capture reagent is immobilized on a support, the tested sample is deposited on the support, and the formation of an immune complex between the support and ADA of the sample, if present, is measured using a tracing reagent. Typically, for determining ADA, the coated or immobilized capture reagent is the drug itself (i.e., the therapeutic antibody). The tracing reagent may be any anti-ADA or ADA-specific reagent, such as an antibody (e.g., a goat or rabbit anti-human Ig antibody), or the drug again. The tracing reagent may be either labeled itself, or detectable through a revealing agent (streptavidin/biotin; peroxidase; enzymatic label, luminescent label, etc).

In a particular embodiment, the capture reagent is the drug itself and the tracing reagent is the biotinylated drug, which can be detected upon incubation of a labeled streptavidin (see FIG. 1).

The capture reagent may be immobilized on the support by various techniques known per se in the art, such as without limitation, adsorption, physical linkage, or chemical binding. Chemical binding may be accomplished e.g., via N-terminal and/or lateral amino groups, and/or via phenolic functional groups or sugar alcohol groups of the reagent to be immobilized (e.g., the drug or an antibody)

The support may be any suitable device, such as a plate (e.g., a multiwell titration plate), a slide, a dish, a tube, a column, etc. The support may also be made of beads.

In another embodiment, the reaction is carried out in solution. In this embodiment, the reagents are not immobilized on a support but directly mixed in solution.

As illustrated in the experimental section, the levels of ADA measured in a sample treated as per the present invention are reliable and stable while, without a pre-treatment to neutralize the antigen, the values obtained are false and unreliable (see FIG. 2).

The invention is particularly suited for assessing the presence of ADA against an anti-TNF drug in a subject. Even more specifically, the invention is particularly adapted to detect ADA against an anti-TNFα therapeutic antibodies including, without limitation, inflimimab, etanercept, adalimumab, golimumab and certolizumab pegol.

Patient Monitoring

Anti-Drug Antibodies ("ADA") diminish, reduce or neutralize the effect of a therapeutic antibody. Accordingly, the detection of these ADA in samples from a subject represents a method of monitoring patients over the course of the treatment as well as a method of improving therapy. When the ADA titer increases, it can be expected that the therapeutic effect of the drug will reduce or be neutralized. In such situations, it is then recommended to change the treatment protocol, e.g., to use a distinct drug.

In a particular aspect, the invention thus relates to a method for detecting the responsiveness of a patient to a therapeutic antibody treatment, the method comprising determining, in a sample from the patient, the presence or amount of Anti-Drug Antibodies directed against said therapeutic antibody using a method as described above; the presence of, or an increase in ADA in the sample being indicative of a loss of responsiveness of the subject.

In another aspect, the invention relates to a method for monitoring a patient undergoing a therapeutic antibody treatment, the method comprising determining, in a sample from the patient, the presence or amount of Anti-Drug Antibodies directed against said therapeutic antibody using a method as described above; the presence of, or an increase in ADA in the sample as compared to a reference value or to a value determined at an earlier stage of treatment being indicative of a loss of responsiveness of the subject to the treatment.

To monitor the subject or assess the responsiveness of the subject, it is even more preferred according to the present invention to measure not only ADA, but also the drug and the antigen in the sample. Indeed, the present application shows that such a combined determination provides a predictive indication of the status of the subject.

Accordingly, the invention also relates to a method for detecting the responsiveness of a patient to a therapeutic antibody treatment, wherein the therapeutic antibody is directed against a target antigen, the method comprising determining, in a sample from the patient, the presence or amount of:

the therapeutic antibody, the antigen, and

Anti-Drug Antibodies directed against said therapeutic antibody; to obtain a patient profile, wherein the patient profile indicates the responsiveness to said treatment.

Preferably, as mentioned in the present invention, the ADA determination should be made after treating the sample to neutralize the antigen. Accordingly, in the above method, if the antigen is detected in the sample, then a further step of determining the presence of said ADA is performed after treatment of the sample to neutralize the antigen.

When the ADA level and/or the level of antigen, increases over a reference value or as compared to a value determined in the subject at an earlier stage of treatment; and when the therapeutic antibody level decreases over a reference value or as compared to a value determined in the subject at an earlier stage of treatment, it can be inferred that the patient is not responding well to the treatment any longer and that the treatment should be adapted. A score of monitoring may also be used as disclosed below, to directly infer from the measures whether the treatment is still adapted to the patient.

The method is preferably performed at different points of time over the course of the treatment of the patient, so that the responsiveness of the patient, or the efficacy of the treatment, can be monitored and, if appropriate, the treatment may be adjusted. In a particular embodiment, the detection can be performed prior to each administration of the therapeutic antibody. Alternatively, the detection may be performed three times at one month interval. For subjects having received therapeutic antibody treatment for a long period of time (e.g., 9 months or more), a single detection according to the invention would be sufficient to qualify the patient as responder or non-responder.

FIG. 5 shows how the profile indicates the responsiveness of the patient, and where treatment should be considered as non effective and changed. As can be determined from FIG. 5, three main situations may be distinguished:

T0: the subject is sick and non treated.

T1-T2: the subject is treated and responds to the treatment. Samples tested by the inventors show that most treated patients fall within this category.

From T3: the subject is treated but does not respond. The therapeutic antibody is neutralized by the ADA. The treatment is not efficient and should be changed.

The therapeutic antibody, antigen, and ADA can be measured by different techniques, including any immunodetection methods such as ELISA, immunocapture, microarrays (protein chips), Flow cytometry (including e.g., Fidis), or multiplex dot, as disclosed above for ADA determination. Typically, all three markers are tested simultaneously (e.g., on the same device). However, determination can be made separately or sequentially.

The invention is particularly suited to monitor patients undergoing anti-TNFα treatment. Such patients typically suffer from an autoimmune or inflammatory disease, such as multiple sclerosis, rheumatoid arthritis, ankylosing spondylitis, Crohn's disease, psoriasis, etc. Monitoring allows regular evaluation of the treatment efficacy and enables the physician to determine whether the treatment may be pursued or should be adapted.

In this regard, evaluation is preferably made by assessing the levels of TNFα, ADA, and anti-TNFα therapeutic antibody in a subject. The values obtained may be either qualitative or quantitative. They may be compared to reference values or to levels registered for the same patient at an earlier stage of treatment. In a particular embodiment, the values are assessed using a "score-table", which allows direct monitoring of the patient.

In a first step, a sample from a patient is tested as disclosed above to quantify the levels of the 3 markers: TNFα, anti-TNFα and ADA. In a second step, using a "score-table", the rate of each parameter is associated to a score. A global score of monitoring is then obtained, consisting of the sum of the score from each parameter: Monitoring score=TNF score+ Anti-TNF score+ADA score.

The score of monitoring may then be compared to (or read with) a monitoring scale, providing the status of the subject. In this respect, the inventors have established monitoring scales suitable to assess the above marker values. These scales are provided below, in relation to anti-TNF therapy. A further scoring scale is disclosed in the examples:

Score-Table for Each Parameter

| Rate of TNF (pg/ml) | <10 | 10 to 100 | >100 |
|---|---|---|---|
| TNF score | 0 | 2 | 5 |
| Rate of Anti-TNF (μg/ml) | <0.5 | 0.5 to 3 | >3 |
| Anti-TNF score | 5 | 3 | 0 |
| Rate of ADA (ng/ml) | <10 | 10 to 100 | >100 |
| ADA score | 0 | 10 | 22 |

Monitoring Scale:

| Monitoring score | Action/Advice |
|---|---|
| 0 to 5 | Continue treatment and monitoring the drug concentration |
| 6 to 10 | Increase anti-TNF |
| 11 to 40 | Consider a switch to another treatment |

As an example, a serum sample from a rheumatoid arthritis patient, treated with Infliximab, is tested according to the invention. The rate of TNFαc, Anti-TNFα, and ADA are 50 pg/ml, <0.1 μg/ml, and 6600 ng/ml, respectively.

The rate of TNFα is associated to a score of 2. The rate of Anti-TNF is associated to a score of 5. The rate of ADA is associated to a score of 22.

The monitoring score is thus 29 and the recommendation for the patient is to switch to another treatment.

The experimental section reports results of testing conducted by the inventors on more than 300 human serum samples from patients undergoing anti-TNFalpha therapy. They show that, following the above method, the status of the patients can reliably be determined and their progression towards a non-responder status can be detected and anticipated. The present invention therefore provides, for the first time, a reliable method for monitoring patients and adjusting their treatment.

Additional Response Markers

In a further preferred embodiment, the methods of the invention comprise combining the above values or scores with additional patient data, which may be either measured or gathered (e.g., from the clinical dossier), to further refine the test. In a particular embodiment, the method of the present invention thus further comprises determining the presence or amount of one or several additional antigens, which may be selected from cytokines, hormones and growth factors, rheumatoid factors, and particular antibodies. Specific, preferred examples of such additional factors include:

Cytokine and chemokines: IL1, IL6, IL8, IL10, ILK12, IL17, IL23, GM-CSF, IFNgamma, ProMPP1 and/or ProMPP3;

Autoimmune antibodies: Antinuclear antibodies (ANA Antibodies to double stranded DNA (dsDNA))

Biological parameters and hematological parameters: C-reactive protein (CRP), RF rheumatoid factor, Serum amyloid A, IgG, IgA, IgM, haemoglobin, erythrocyte sedimentation rate (ESR), white cells and platelet counts, numbers of CD19-B cells, number of CD3_, CD4_, CD8_, CD4_, CD25_, and/or CD8_, HLA-DR_T cells Patient parameters: such as sex, VS, age or DAS28. weight, Treatment parameter: posology Biomarker concentrations (TNF, anti-TNF and ADA) are measured using a quantitative immunoassay and combined with the additional parameters from the clinical data set to generate the score of monitoring. The algorithm uses different weightings (Wn) to assess treatment efficacy (monitoring score). The resulting monitoring score is scaled so that each test result is a decimal number between 1 to 10. As an example, the algorithm of the score of monitoring is the following:

$$\text{Monitoring Score} = W1 \times \{TNF\} + W2 \times \{\text{anti-TNF}\} + W3 \times \{ADA\} + W4 \times \{CRP\} + W5 \times \{ESR\}.$$

Wn: is the weighting for each parameter, according to the importance of these parameters on the treatment impact.

{TNF}: scoring factor of TNF. TNF impact on the score of monitoring according to the concentration of TNF measured.

{anti-TNF}: scoring factor of anti-TNF. Anti-TNF impact on the score of monitoring, according to the concentration of anti-TNF measured. The scoring factor o anti-TNF is "posology" dependent (information available in the clinical data set).

{ADA}: scoring factor of ADA. ADA impact on the score of monitoring, according to the concentration of ADA measured.

{CRP}: scoring factor of CRP. CRP impact on the score of monitoring, according to the concentration of C-reactive protein provided by the clinical data set.

{ESR}: scoring factor of ESR. ESR impact on the score of monitoring, according to erythrocyte sedimentation rate, provided by the clinical data set. The Sedimentation rate is "age and sex" dependent; information in the clinical data set).

The score of monitoring is intended to be used in conjunction with the whole clinical data set to help the physician in their decision about the course of the treatment. The monitoring score is a number scaled between 1 and 10. According to the score of monitoring, interpretation of treatment efficacy can be done, e.g., as shown FIG. 6.

Inactive TNFalpha as a Marker of Treatment Switch

We have determined the biological activity of TNFalpha detected is patients which do not respond to the treatment (see area T3 and T4 of FIG. 5). The activity was detected by evaluating target cell lysis upon exposure to the TNFalpha samples. Our results surprisingly show that this TNFalpha is biologically inactive. These results were totally unexpected and it had never been reported that patients undergoing anti-TNFalpha treatment had circulating inactive TNFalpha. Our results further show that inactive TNFalpha levels correlate with the lack of response of patients to their anti-TNF treatment. The presence of such inactive TNFalpha is intriguing. We hypothesise that TNFalpha is first captured by anti-TNAalpha therapeutic antibodies, and subsequently released when ADA bind to the therapeutic antibody molecules. TNFalpha released from ADA would be inactive (or inactivated) as a result of conformational or structural alteration(s) caused by ADA binding.

Dosing of inactive TNFalpha in patients undergoing anti-TNF therapy therefore represents a novel and very reliable means to determine patient responsiveness, and to adjust treatment (e.g., switch treatment to another therapeutic antibody or to another class of treatment).

In a particular embodiment, the invention therefore relates to a method for detecting the responsiveness of a patient to a therapeutic antibody treatment, wherein the therapeutic antibody is directed against TNFalpha, the method comprising determining, in a sample from the patient, the presence or amount of inactive TNFalpha, said presence or amount being indicative of low or decreasing responsiveness of the patient to said treatment.

In a particular embodiment, the invention also relates to a method for monitoring a patient undergoing anti-TNFalpha treatment, the method comprising determining, in a sample from the patient, the presence or amount of inactive TNFalpha, said presence or amount being indicative of the responsiveness of the patient to said treatment. Appearance of inactive TNalpha is an indication that the subject begins to escape treatment. Increasing levels of such inactive TNFalpha indicates the patient should be switched to another treatment.

"Inactive TNFalpha" designates, in this context, a TNFalpha which does not cause target cell lysis in vitro. Inactive TNFalpha more specifically includes inactivated TNFalpha, e.g., Antibody-inactivated TNFalpha. In the above embodiments, the method may further comprise a step of detecting the biological activity of the TNFalpha in the tested sample. Alternatively, or in addition, the method may comprise a step of detecting the structure of an inactive TNFalpha molecule.

In a preferred embodiment, the above method also comprises a determination of the presence or amount of the anti-TNFalpha therapeutic antibody and Anti-Drug Antibodies to obtain a patient profile, wherein the patient profile indicates the responsiveness to said treatment. In a further preferred embodiment, the method further comprises detecting additional parameters as specified above.

A further object of the invention is a kit comprising:
- one or several reagents to detect, in a sample, the presence or amount of Anti-Drug Antibodies directed against a therapeutic antibody;
- one or several reagents to neutralize the target antigen of said therapeutic antibody in the sample.

In a preferred embodiment, the invention relates to an enzyme linked immunoassay (ELISA) kit or method for the combined quantitative determination of human TNFα, an anti-TNFα Drug (preferably infliximab, etanercept, adalimumab, golimumab or certolizumab pegol) and corresponding ADA in human serum samples. This kit allows the physician to monitor the evolution of the rate of these 3 parameters in patient sera.

Further aspects and advantages of the invention will be disclosed in the following experimental section, which should be considered as illustrative only.

EXAMPLES

In the experimental section, every dosage is quantitative, calibrated with regard to standards. Dosage of TNF (pg/ml) is made with the help of the international standard. Dosage of the drug (μg/ml) is made thanks to the concentration value given by the pharma company. Dosage of ADA (ng/ml) is made using a rabbit polyclonal antibody as a standard. Rabbits (origin Hyla) are immunized with Fab or Fab'2 fragments of the anti-TNF immunoglobulins or with human P75 TNF receptor. Quantification of the ADA human standard is obtained by the method of the biuret (dosage of protein by colorimetry).

Example A

Method of Detecting ADA

The drug is coated onto a polystyrene microtiter plate.
First, an acid solution, such acid acetic solution, is added to the sample. The acidified sample is incubated at room temperature for approximately 5 minutes.
Then, a basic solution, such as TRIS solution, is added to the acidified sample to neutralize acid solution.
Then, sample (diluted or not) is added to the antibody coated well, which allows to bind. After incubation, unbound proteins are removed by washing.
Biotinylated drug is added. After incubation, unbound antibodies are removed by washing.
Then horseradish peroxidase labelled streptavidin is added. The streptavidin binds to the complex formed with biotinylated drug. After incubation, the wells are washed again to eliminate any excess of conjugate.
The bound enzyme is revealed by addition of substrate TMB (3,3',5,5' tetramethylbenzidin). The colour intensity is proportional to the amount of anti-Etanercept antibodies.
Adding $H_2SO_4$ (0.25M) allows to stop the enzymatic reaction.
After stopping the reaction by $H_2SO_4$ (0.25M), the optical density is read by a spectrophotometer at 450 nm.
A range of calibration allows to define the quantity of anti-drug antibodies of each patient samples expressed in ng/mL.

The principle of the test is depicted FIG. 1. The results are shown FIG. 2.

The results surprisingly show that, when the antigen is present in the sample, the quantification of ADA is drastically over-estimated. In contrast, after neutralization of the antigen by acid treatment, the quantification of ADA is correct and reliable. The presence of the antigen during the dosage of ADA involves an erroneous dosage in ADA, which could give rise to wrongly positive results. Consequently, during a positive dosage in antigen, it is necessary to proceed to a second test ADA after neutralization to obtain Ada's correct result.

Example B

Method and Kit for Monitoring Patients Treated with Etanercept

The test should be performed on serum or on plasma. TNFα being unstable in solution, it is preferred to use samples immediately after blood taking. If determination is not performed immediately, samples should be frozen. To avoid any non-specific binding, samples which have been frozen for more than 6 months or which are cloudy, should be centrifuged and filtered.

1. Dosage of TNFα

A monoclonal anti-TNFα antibody is coated onto a polystyrene microtiter plate (4 strips of 8 wells).
First, the diluted sample is added to the antibody coated well, which allows to bind. After incubation, unbound proteins are removed by washing.
Anti-TNFα biotinylated antibody is added. After incubation, unbound antibodies are removed by washing
Then horseradish peroxydase labelled streptavidin is added. The streptavidin binds to the complex formed with biotinylated anti-TNFα antibodies. After incubation, the wells are washed again to eliminate any excess of conjugate.
The bound enzyme is revealed by addition of substrate TMB (3,3',5,5' tetramethylbenzidin). The colour intensity is proportional to the amount of TNFα.
Adding $H_2SO_4$ (0.25M) allows to stop the enzymatic reaction.
After stopping the reaction by $H_2SO_4$ (0.25M), the optical density is read by a spectrophotometer at 450 nm.
A range of calibration allows to define the quantity of TNFα of each patient samples expressed in pg/mL.

2. Dosage of Etanercept

The TNFα is coated onto a polystyrene microtiter plate (4 strips of 8 wells).
First, the diluted sample is added to the antibody coated well, which allows to bind. After incubation, unbound proteins are removed by washing.
Anti-human IgG biotinylated antibody is added. After incubation, unbound antibodies are removed by washing
Then horseradish peroxidase labelled streptavidin is added. The streptavidin binds to the complex formed with biotinylated anti-IgG antibodies. After incubation, the wells are washed again to eliminate any excess of conjugate.
The bound enzyme is revealed by addition of substrate TMB (3,3',5,5' tetramethylbenzidin). The colour intensity is proportional to the amount of Etanercept.
Adding $H_2SO_4$ (0.25M) allows to stop the enzymatic reaction.
After stopping the reaction by $H_2SO_4$ (0.25M), the optical density is read by a spectrophotometer at 450 nm.
A range of calibration allows to define the quantity of Etanercept of each patient samples expressed in µg/mL.

3. Dosage of Anti-Etanercept

The Etanercept is coated onto a polystyrene microtiter plate (4 strips of 8 wells).
First, the diluted sample is added to the antibody coated well, which allows to bind. After incubation, unbound proteins are removed by washing.
Biotinylated Etanercept is added. After incubation, unbound antibodies are removed by washing
Then horseradish peroxidase labelled streptavidin is added. The streptavidin binds to the complex formed with biotinylated Etanercept. After incubation, the wells are washed again to eliminate any excess of conjugate.
The bound enzyme is revealed by addition of substrate TMB (3,3',5,5' tetramethylbenzidin). The colour intensity is proportional to the amount of anti-Etanercept antibodies.
Adding $H_2SO_4$ (0.25M) allows to stop the enzymatic reaction.
After stopping the reaction by $H_2SO_4$ (0.25M), the optical density is read by a spectrophotometer at 450 nm.
A range of calibration allows to define the quantity of anti-Etanercept antibodies of each patient samples expressed in ng/mL.

4. Results

During the course of the treatment, the evolution of the rate of the 3 parameters (TNF, Etanercept, Anti-Etanercept) has been monitored according to the present invention in a human subject. Serum samples from a Rheumatoid patient (patient1)

were tested before the first infusion of Etanercept The results are depicted below:

|  | TNF (pg/ml) | Etanercept (µg/ml) | Anti-Etanercept |
|---|---|---|---|
| Patient 1, W0 | <10 | <0.2 | <5 |
| Patient 1, W8 | 117 | 1.7 | <5 |

These results show that the level of TNF and the level of Etanercept increase during the course of treatment.

Example C

Method and Kit for Monitoring Patients Treated with Adalimumab

The test was performed on serum or on plasma. TNFα being unstable in solution, samples were used immediately after blood taking or frozen. To avoid any non-specific binding, samples which had been frozen for more than 6 months or which were cloudy, were centrifuged and filtered.

1. Dosage of TNFα

A monoclonal anti-TNFα antibody is coated onto a polystyrene microtiter plate (4 strips of 8 wells).

First, the diluted sample is added to the antibody coated well, which allows to bind. After incubation, unbound proteins are removed by washing.

Anti-TNFα biotinylated antibodies is added. After incubation, unbound antibodies are removed by washing Then horseradish peroxidase labelled streptavidin is added. The streptavidin binds to the complex formed with biotinylated anti-TNFα antibodies. After incubation, the wells are washed again to eliminate any excess of conjugate.

The bound enzyme is revealed by addition of substrate TMB (3,3',5,5' tetramethylbenzidin). The colour intensity is proportional to the amount of TNFα.

Adding $H_2SO_4$ (0.25M) allows to stop the enzymatic reaction.

After stopping the reaction by $H_2SO_4$ (0.25M), the optical density is read by a spectrophotometer at 450 nm.

A range of calibration allows to define the quantity of TNFα of each patient samples expressed in pg/mL.

2. Dosage of Adalimumab

TNFα is coated onto a polystyrene microtiter plate (4 strips of 8 wells).

First, the diluted sample is added to the antibody coated well, which allows to bind. After incubation, unbound proteins are removed by washing.

Anti-human IgG biotinylated antibodies is added. After incubation, unbound antibodies are removed by washing Then horseradish peroxidase labelled streptavidin is added. The streptavidin binds to the complex formed with biotinylated anti-IgG antibodies. After incubation, the wells are washed again to eliminate any excess of conjugate.

The bound enzyme is revealed by addition of substrate TMB (3,3',5,5' tetramethylbenzidin). The colour intensity is proportional to the amount of Adalimumab.

Adding $H_2SO_4$ (0.25M) allows to stop the enzymatic reaction.

After stopping the reaction by $H_2SO_4$ (0.25M), the optical density is read by a spectrophotometer at 450 nm.

A range of calibration allows to define the quantity of Adalimumab of each patient samples expressed in µg/mL.

3. Dosage of Anti-Adalimumab

The Adalimumab is coated onto a polystyrene microtiter plate (4 strips of 8 wells).

First, the diluted sample is added to the antibody coated well, which allows to bind. After incubation, unbound proteins are removed by washing.

Biotinylated Adalimumab is added. After incubation, unbound antibodies are removed by washing Then horseradish peroxidase labelled streptavidin is added. The streptavidin binds to the complex formed with biotinylated Adalimumab. After incubation, the wells are washed again to eliminate any excess of conjugate.

The bound enzyme is revealed by addition of substrate TMB (3,3',5,5' tetramethylbenzidin). The colour intensity is proportional to the amount of anti-Adalimumab antibodies.

Adding $H_2SO_4$ (0.25M) allows to stop the enzymatic reaction.

After stopping the reaction by $H_2SO_4$ (0.25M), the optical density is read by a spectrophotometer at 450 nm.

A range of calibration allows to define the quantity of anti-Adalimumab antibodies of each patient samples expressed in ng/mL.

4. Results

During the course of the treatment, the evolution of the rate of the 3 parameters (TNF, Adalimumab, Anti-Adalimumab) has been monitored using the invention.

Serum samples from a Rheumatoid arthritis patient (patient2) were tested before the first infusion of Adalimumab (W0) and before subsequent infusions of Adalimumab (W6, W21, W30, W39).

|  | TNF (pg/ml) | Adalimumab (µg/ml) | Anti-Adalimumab (ng/ml) |
|---|---|---|---|
| Patient 2, W0 | <10 | <0.1 | <10 |
| Patient 2, W6 | <10 | 6.4 | <10 |
| Patient 2, W21 | <10 | 16.8 | <10 |
| Patient 2, W30 | <10 | 16.7 | <10 |
| Patient 2, W39 | <10 | 17.1 | <10 |

The above table shows that the level of Adalimumab increased in said patient during the course of treatment to reach a level about 17 µg/ml. The level of TNF and the level of Anti-Adalimumab did not increase.

Example D

Method and Kit for Monitoring Patients Treated with Infliximab

The test was performed on serum or on plasma. TNFα being unstable in solution, samples were used immediately after blood taking or frozen. To avoid any non-specific binding, samples which had been frozen for more than 6 months or which were cloudy, were centrifuged and filtered.

1. Dosage of TNFα

A monoclonal anti-TNFα antibody is coated onto a polystyrene microtiter plate (4 strips of 8 wells).

First, the diluted sample is added to the antibody coated well, which allows to bind. After incubation, unbound proteins are removed by washing.

Anti-TNFα biotinylated antibodies is added. After incubation, unbound antibodies are removed by washing Then horseradish peroxidase labelled streptavidin is added. The streptavidin binds to the complex formed with biotinylated anti-TNFα antibodies. After incubation, the wells are washed again to eliminate any excess of conjugate.

The bound enzyme is revealed by addition of substrate TMB (3,3',5,5' tetramethylbenzidin). The colour intensity is proportional to the amount of TNFα.

Adding $H_2SO_4$ (0.25M) allows to stop the enzymatic reaction.

After stopping the reaction by $H_2SO_4$ (0.25M), the optical density is read by a spectrophotometer at 450 nm.

A range of calibration allows to define the quantity of TNFα of each patient samples expressed in pg/mL.

2. Dosage of Infliximab

The TNFα is coated onto a polystyrene microtiter plate (4 strips of 8 wells).

First, the diluted sample is added to the antibody coated well, which allows to bind. After incubation, unbound proteins are removed by washing.

Anti-human IgG biotinylated antibodies is added. After incubation, unbound antibodies are removed by washing Then horseradish peroxidase labelled streptavidin is added. The streptavidin binds to the complex formed with biotinylated anti-IgG antibodies. After incubation, the wells are washed again to eliminate any excess of conjugate.

The bound enzyme is revealed by addition of substrate TMB (3,3',5,5' tetramethylbenzidin). The colour intensity is proportional to the amount of Infliximab.

Adding $H_2SO_4$ (0.25M) allows to stop the enzymatic reaction.

After stopping the reaction by $H_2SO_4$ (0.25M), the optical density is read by a spectrophotometer at 450 nm.

A range of calibration allows to define the quantity of Infliximab of each patient samples expressed in μg/mL.

3. Dosage of Anti-Infliximab

Infliximab is coated onto a polystyrene microtiter plate (4 strips of 8 wells).

First, the diluted sample is added to the antibody coated well, which allows to bind. After incubation, unbound proteins are removed by washing.

Biotinylated Infliximab is added. After incubation, unbound antibodies are removed by washing Then horseradish peroxidase labelled streptavidin is added. The streptavidin binds to the complex formed with biotinylated Infliximab. After incubation, the wells are washed again to eliminate any excess of conjugate.

The bound enzyme is revealed by addition of substrate TMB (3,3',5,5' tetramethylbenzidin). The colour intensity is proportional to the amount of anti-Infliximab antibodies.

Adding $H_2SO_4$ (0.25M) allows to stop the enzymatic reaction.

After stopping the reaction by $H_2SO_4$ (0.25M), the optical density is read by a spectrophotometer at 450 nm.

A range of calibration allows to define the quantity of anti-Infliximab antibodies of each patient samples expressed in ng/mL.

4. Results

During the course of the treatment, the evolution of the rate of the 3 parameters (TNF, Infliximab, Anti-Infliximab) has been monitored in human subjects.

In a first Rheumatoid arthritis patient (patient 3), serum samples were tested before the second infusion of Infliximab (W2) and before the subsequent infusions of Infliximab (W6, W14, W28, W42, W56).

|  | TNF (pg/ml) | Infliximab (μg/ml) | Anti-Infliximab (ng/ml) |
| --- | --- | --- | --- |
| Patient 3, W2 | <10 | <0.1 | <10 |
| Patient 3, W6 | <10 | <0.1 | 266 |
| Patient 3, W14 | <10 | <0.1 | 172 |
| Patient 3, W28 | <10 | <0.1 | 192 |
| Patient 3, W42 | <10 | <0.1 | 491 |
| Patient 3, W56 | <10 | <0.1 | 253 |

The results show that the level of Anti-Infliximab increased during the course of treatment, to reach a high level (>100 ng/ml). The level of TNF and the level of Anti-Infliximab were undetectable.

In another Rheumatoid patient (patient4), serum samples were tested before the second infusion of Infliximab (W2) and before the third infusion of Infliximab (W5).

|  | TNF (pg/ml) | Infliximab (μg/ml) | Anti-Infliximab (ng/ml) |
| --- | --- | --- | --- |
| Patient 4, W2 | <10 | 20.1 | <10 |
| Patient 4, W5 | 50 | <0.1 | 6600 |

The results show that the level of Anti-Infliximab increased during the course of treatment, to reach a high level (>100 ng/ml). The level of TNF increase to 50 pg/ml and the level of Infliximab drops below 0.1 μg/ml.

Example E

Method and Kit for Monitoring Patients Treated with Certolizumab

The test was performed on serum or on plasma. TNFα being unstable in solution, samples were used immediately after blood taking or frozen. To avoid any non-specific binding, samples which had been frozen for more than 6 months or which were cloudy, were centrifuged and filtered.

1. Dosage of TNFα

A monoclonal anti-TNFα antibody is coated onto a polystyrene microtiter plate (4 strips of 8 wells).

First, the diluted sample is added to the antibody coated well, which allows to bind. After incubation, unbound proteins are removed by washing.

Anti-TNFα biotinylated antibodies is added. After incubation, unbound antibodies are removed by washing Then horseradish peroxidase labelled streptavidin is added. The streptavidin binds to the complex formed with biotinylated anti-TNFα antibodies. After incubation, the wells are washed again to eliminate any excess of conjugate.

The bound enzyme is revealed by addition of substrate TMB (3,3',5,5' tetramethylbenzidin). The colour intensity is proportional to the amount of TNFα.

Adding $H_2SO_4$ (0.25M) allows to stop the enzymatic reaction.

After stopping the reaction by $H_2SO_4$ (0.25M), the optical density is read by a spectrophotometer at 450 nm.

A range of calibration allows to define the quantity of TNFα of each patient samples expressed in pg/mL.

2. Dosage of Certolizumab

The TNFα is coated onto a polystyrene microtiter plate (4 strips of 8 wells).

First, the diluted sample is added to the antibody coated well, which allows to bind. After incubation, unbound proteins are removed by washing.

Biotinylated anti-PEG antibody is added. After incubation, unbound antibodies are removed by washing Then horseradish peroxidase labelled streptavidin is added. The streptavidin binds to the complex formed with biotinylated anti-PEG antibody. After incubation, the wells are washed again to eliminate any excess of conjugate.

The bound enzyme is revealed by addition of substrate TMB (3,3',5,5' tetramethylbenzidin). The colour intensity is proportional to the amount of Infliximab.

Adding $H_2SO_4$ (0.25M) allows to stop the enzymatic reaction.

After stopping the reaction by $H_2SO_4$ (0.25M), the optical density is read by a spectrophotometer at 450 nm.

A range of calibration allows to define the quantity of Certolizumab of each patient samples expressed in μg/mL.

3. Dosage of Anti-Certolizumab

Certolizumab is coated onto a polystyrene microtiter plate (4 strips of 8 wells).

First, the diluted sample is added to the antibody coated well, which allows to bind. After incubation, unbound proteins are removed by washing.

Biotinylated certolizumab is added. After incubation, unbound antibodies are removed by washing Then horseradish peroxidase labelled streptavidin is added. The streptavidin binds to the complex formed with biotinylated Certolizumab. After incubation, the wells are washed again to eliminate any excess of conjugate.

The bound enzyme is revealed by addition of substrate TMB (3,3',5,5' tetramethylbenzidin). The colour intensity is proportional to the amount of anti-Infliximab antibodies.

Adding $H_2SO_4$ (0.25M) allows to stop the enzymatic reaction.

After stopping the reaction by $H_2SO_4$ (0.25M), the optical density is read by a spectrophotometer at 450 nm.

A range of calibration allows to define the quantity of anti-Certolizumab antibodies of each patient samples expressed in ng/mL.

4. Dosage of Anti-Certolizumab (Alternative)

Certolizumab is coated onto a polystyrene microtiter plate (4 strips of 8 wells).

First, the diluted sample is added to the antibody coated well, which allows to bind. After incubation, unbound proteins are removed by washing.

Biotinylated anti-human IgG and biotinylated anti-human IgM are added. After incubation, unbound antibodies are removed by washing Then horseradish peroxidase labelled streptavidin is added. The streptavidin binds to the complex formed with biotinylated anti-human IgG and anti-human IgM. After incubation, the wells are washed again to eliminate any excess of conjugate.

The bound enzyme is revealed by addition of substrate TMB (3,3',5,5' tetramethylbenzidin). The colour intensity is proportional to the amount of anti-Infliximab antibodies.

Adding $H_2SO_4$ (0.25M) allows to stop the enzymatic reaction.

After stopping the reaction by $H_2SO_4$ (0.25M), the optical density is read by a spectrophotometer at 450 nm.

A range of calibration allows to define the quantity of anti-Certolizumab antibodies of each patient samples expressed in ng/mL.

Example F

Method and Kit for Monitoring Patients Treated with Golimumab

The test was performed on serum or on plasma. TNFα being unstable in solution, samples were used immediately after blood taking or frozen. To avoid any non-specific binding, samples which had been frozen for more than 6 months or which were cloudy, were centrifuged and filtered.

1. Dosage of TNFα

A monoclonal anti-TNFα antibody is coated onto a polystyrene microtiter plate (4 strips of 8 wells).

First, the diluted sample is added to the antibody coated well, which allows to bind.

After incubation, unbound proteins are removed by washing.

Anti-TNFα biotinylated antibodies is added. After incubation, unbound antibodies are removed by washing Then horseradish peroxidase labelled streptavidin is added. The streptavidin binds to the complex formed with biotinylated anti-TNFα antibodies. After incubation, the wells are washed again to eliminate any excess of conjugate.

The bound enzyme is revealed by addition of substrate TMB (3,3',5,5' tetramethylbenzidin). The colour intensity is proportional to the amount of TNFα.

Adding $H_2SO_4$ (0.25M) allows to stop the enzymatic reaction.

After stopping the reaction by $H_2SO_4$ (0.25M), the optical density is read by a spectrophotometer at 450 nm.

A range of calibration allows to define the quantity of TNFα of each patient samples expressed in pg/mL.

2. Dosage of Golimumab

The TNFα is coated onto a polystyrene microtiter plate (4 strips of 8 wells).

First, the diluted sample is added to the antibody coated well, which allows to bind. After incubation, unbound proteins are removed by washing.

Anti-human IgG biotinylated antibodies is added. After incubation, unbound antibodies are removed by washing Then horseradish peroxidase labelled streptavidin is added. The streptavidin binds to the complex formed with biotinylated anti-IgG antibodies. After incubation, the wells are washed again to eliminate any excess of conjugate.

The bound enzyme is revealed by addition of substrate TMB (3,3',5,5' tetramethylbenzidin). The colour intensity is proportional to the amount of Infliximab.

Adding $H_2SO_4$ (0.25M) allows to stop the enzymatic reaction.

After stopping the reaction by $H_2SO_4$ (0.25M), the optical density is read by a spectrophotometer at 450 nm.

A range of calibration allows to define the quantity of Golimumab of each patient samples expressed in μg/mL.

3. Dosage of Anti-Golimumab

Infliximab is coated onto a polystyrene microtiter plate (4 strips of 8 wells).

First, the diluted sample is added to the antibody coated well, which allows to bind. After incubation, unbound proteins are removed by washing.

Biotinylated Golimumab is added. After incubation, unbound antibodies are removed by washing Then horseradish peroxidase labelled streptavidin is added. The streptavidin binds to the complex formed with biotinylated Golimumab. After incubation, the wells are washed again to eliminate any excess of conjugate.

The bound enzyme is revealed by addition of substrate TMB (3,3',5,5' tetramethylbenzidin). The colour intensity is proportional to the amount of anti-Infliximab antibodies.

Adding $H_2SO_4$ (0.25M) allows to stop the enzymatic reaction.

After stopping the reaction by $H_2SO_4$ (0.25M), the optical density is read by a spectrophotometer at 450 nm.

A range of calibration allows to define the quantity of anti-Golimumab antibodies of each patient samples expressed in ng/mL.

Example G

Biological Activity of TNFalpha

TNF activity was assessed by using the L929 cytotoxic assay (Bloquel C. et al. (2004) *Hum Gene Ther.* 15:189-201). Serial dilutions of TNF serum samples were incubated with L929 cells and the number of surviving cells determined by the MTT dying assay.

The results show that TNFalpha from treated patients is inactive, i.e., does not cause substantial lysis of L929 cells.

Example H

Validation of the Method on a Cohort of Above 300 Human Patients

The test was performed on serum or on plasma. TNFα being unstable in solution, samples were used immediately after blood taking or frozen. To avoid any non-specific binding, samples which had been frozen for more than 6 months or which were cloudy, were centrifuged and filtered. For each patient, detection was conducted at different points of time during treatment.

1. Dosage of TNFα

A monoclonal anti-TNFα antibody is coated onto a polystyrene microtiter plate (4 strips of 8 wells).

First, the diluted sample is added to the antibody coated well, which allows to bind. After incubation, unbound proteins are removed by washing.

Anti-TNFα biotinylated antibodies is added. After incubation, unbound antibodies are removed by washing Then horseradish peroxidase labelled streptavidin is added. The streptavidin binds to the complex formed with biotinylated anti-TNFα antibodies. After incubation, the wells are washed again to eliminate any excess of conjugate.

The bound enzyme is revealed by addition of substrate TMB (3,3',5,5' tetramethylbenzidin). The colour intensity is proportional to the amount of TNFα.

Adding $H_2SO_4$ (0.25M) allows to stop the enzymatic reaction.

After stopping the reaction by $H_2SO_4$ (0.25M), the optical density is read by a spectrophotometer at 450 nm.

A range of calibration allows to define the quantity of TNFα of each patient samples expressed in pg/mL.

2. Dosage of Infliximab

The TNFα is coated onto a polystyrene microtiter plate (4 strips of 8 wells).

First, the diluted sample is added to the antibody coated well, which allows to bind. After incubation, unbound proteins are removed by washing.

Anti-human IgG biotinylated antibodies is added. After incubation, unbound antibodies are removed by washing Then horseradish peroxidase labelled streptavidin is added. The streptavidin binds to the complex formed with biotinylated anti-IgG antibodies. After incubation, the wells are washed again to eliminate any excess of conjugate.

The bound enzyme is revealed by addition of substrate TMB (3,3',5,5' tetramethylbenzidin). The colour intensity is proportional to the amount of Infliximab.

Adding $H_2SO_4$ (0.25M) allows to stop the enzymatic reaction.

After stopping the reaction by $H_2SO_4$ (0.25M), the optical density is read by a spectrophotometer at 450 nm.

A range of calibration allows to define the quantity of Infliximab of each patient samples expressed in µg/mL.

3. Dosage of Anti-Infliximab

Infliximab is coated onto a polystyrene microtiter plate (4 strips of 8 wells).

First, the diluted sample is added to the antibody coated well, which allows to bind. After incubation, unbound proteins are removed by washing.

Biotinylated Infliximab is added. After incubation, unbound antibodies are removed by washing Then horseradish peroxidase labelled streptavidin is added. The streptavidin binds to the complex formed with biotinylated Infliximab. After incubation, the wells are washed again to eliminate any excess of conjugate.

The bound enzyme is revealed by addition of substrate TMB (3,3',5,5' tetramethylbenzidin). The colour intensity is proportional to the amount of anti-Infliximab antibodies.

Adding $H_2SO_4$ (0.25M) allows to stop the enzymatic reaction.

After stopping the reaction by $H_2SO_4$ (0.25M), the optical density is read by a spectrophotometer at 450 nm.

A range of calibration allows to define the quantity of anti-Infliximab antibodies of each patient samples expressed in ng/mL.

4. Additional Parameters

[CRP]: CRP concentration, expressed mg/L

ESR: erythrocyte sedimentation rate, expressed in mm/h

Posology: to know if the posology is normal, or if the posology is higher than the normal posology.

Age, sex, weight.

5. Scoring Factors:

{TNF}: scoring factor of TNF, according to the concentration of TNF measured. As an example:

The scoring factor for a measured sample below 10 pg/ml is: 1

The scoring factor for a measured sample between 10 and 100 pg/ml is: 4.

The scoring factor for a measured sample upper 100 pg/ml is: 10.

{anti-TNF}: scoring factor of anti-TNF, according to the concentration of anti-TNF measured.

For a patient with normal posology:

The scoring factor for a measured sample below 0.1 µg/ml: 10

The scoring factor for a measured sample between 0.1 and 0.5 µg/ml: 6

The scoring factor for a measured sample between 0.5 and 1.8 µg/ml is: 4

The scoring factor for a measured sample upper 1.8 µg/ml: 1

For a patient with augmented posology:
The scoring factor for a measured sample below 0.1 μg/ml: 12.5
The scoring factor for a measured sample between 0.1 and 0.5 μg/ml: 10
The scoring factor for a measured sample between 0.5 and 1.8 μg/ml is: 7.5
The scoring factor for a measured sample upper 1.8 μg/ml: 1.25
{ADA}: scoring factor of ADA, according to the concentration of ADA measured.
The scoring factor for a measured sample below 10 ng/ml: 1
The scoring factor for a measured sample between 10 and 200 ng/ml: 5
The scoring factor for a measured sample upper 200 ng/ml: 10
{CRP}: scoring factor of CRP, according to the concentration of C-reactive protein provided by the clinical data set.
The scoring factor for a measured sample below 6 mg/L: 1
The scoring factor for a measured sample between 6 and 50 mg/L: 4
The scoring factor for a measured sample upper 50 mg/L: 10
{ESR}: scoring factor of ESR, according to erythrocyte sedimentation rate, provided by the clinical data set. The Sedimentation rate is "age and sex" dependent).
The scoring factor for a measured sample below 15 mm/h: 1
The scoring factor for a measured sample between 15 and 20 mm/h: 4
The scoring factor for a measured sample upper 20 mm/h: 10

6. Weightings

Every scoring factor from each parameter is associated to a weighting factor (Wn) according to the impact of these parameters on the treatment.

As an example:
The weighting factor of TNF is: 15%
The weighting factor of anti-TNF is: 30%
The weighting factor of ADA is: 35%
The weighting factor of CRP is: 10%
The weighting factor of ESR is: 10%

7. Results:

7.1. Analysis of Rheumatoid Arthritis Patients Treated with Infliximab

We tested serum samples from Rheumatoid Arthritis patient treated with Infliximab at different times during the course of the treatment. The figures in Table A below show, for each patient:
- the measured level of: TNF, anti-TNF (Infliximab), and ADA (anti-infliximab).
- the information from the clinical data set: CRP, ESR and posology,
- the scoring factor for each parameter
- the weighting factor for each parameter.
- the result of the score of monitoring
- the patient response to the treatment according to the whole clinical data set: response (R), no-response or incomplete response (NR), beginning of treatment (T0).

Consecutive results for each patient represent measures at different points during treatment.

TABLE A

| | Measured level of: | | | clinical data set | | | scoring factors | | | |
|---|---|---|---|---|---|---|---|---|---|---|
| Patient | TNF | Infliximab | ADA | CRP | posology | VS | TNF | Infliximab | ADA | CRP |
| 7 | 0 | 0 | 0 | 6 | norm. | 9 | 1 | 10 | 1 | 1 |
| 7 | 0 | 11.5 | 0 | 5.4 | norm. | 10 | 1 | 1 | 1 | 1 |
| 7 | 0 | 1.3 | 0 | 5 | norm. | 5 | 1 | 3 | 1 | 1 |
| 20 | 0 | 0.0 | 67 | 5 | norm. | 9 | 1 | 10 | 4 | 1 |
| 20 | 0 | 0.0 | 701 | 5 | norm. | 16 | 1 | 10 | 10 | 1 |
| 20 | 0 | 0.0 | 42 | 5 | norm. | 26 | 1 | 10 | 4 | 1 |
| 20 | 0 | 0.0 | 23 | 5 | norm. | 20 | 1 | 10 | 4 | 1 |
| 21 | 0 | 0.0 | 0 | 5 | norm. | 25 | 1 | 10 | 1 | 1 |
| 21 | 0 | 2.3 | 0 | 5.1 | norm. | 53 | 1 | 1 | 1 | 1 |
| 21 | 0.0 | 2.4 | 0.0 | 5 | norm. | 34 | 1 | 1 | 1 | 1 |
| 21 | 0 | 2.2 | 0 | 5 | norm. | 22 | 1 | 1 | 1 | 1 |
| 31 | 0 | 2.4 | 0 | 5 | norm. | 8 | 1 | 1 | 1 | 1 |
| 31 | 0.0 | 2.4 | 0.0 | 5 | norm. | 1 | 1 | 1 | 1 | 1 |
| 31 | 0 | 0.0 | 47 | 11.4 | norm. | 21 | 1 | 10 | 4 | 4 |
| 47 | 0 | 5.8 | 0 | 5 | norm. | 6 | 1 | 1 | 1 | 1 |
| 47 | 0 | 93.4 | 0 | 5 | norm. | 9 | 1 | 1 | 1 | 1 |
| 47 | 0 | 6.5 | 0 | 5 | norm. | 4 | 1 | 1 | 1 | 1 |
| 47 | 0 | 4.1 | 0 | 5 | norm. | 5 | 1 | 1 | 1 | 1 |
| 49 | 0 | 5.2 | 0 | 24 | aug. | 43 | 1 | 1 | 1 | 4 |
| 49 | 0.0 | 5.2 | 0.0 | 6 | aug. | | 1 | 1 | 1 | 1 |
| 49 | 0 | 0.0 | 0 | 22 | aug. | 54 | 1 | 10 | 1 | 4 |
| 58 | 0 | 2.7 | 0 | 5 | norm. | 3 | 1 | 1 | 1 | 1 |
| 58 | 0 | 0.6 | 0 | 5 | norm. | 3 | 1 | 3 | 1 | 1 |
| 58 | 0 | 1.9 | 0 | 6 | norm. | 5 | 1 | 1 | 1 | 1 |
| 67 | 75 | 0.0 | 54 | 15.5 | norm. | 25 | 4 | 10 | 4 | 4 |
| 67 | 10 | 24.0 | 0.0 | 5 | norm. | 2 | 4 | 1 | 1 | 1 |
| 67 | 11 | 11.4 | 0 | 5 | norm. | 3 | 4 | 1 | 1 | 1 |
| 67 | 0 | 9.9 | 0 | 5 | norm. | 3 | 1 | 1 | 1 | 1 |
| 86 | 0 | 0.0 | 0 | 6 | norm. | 9 | 1 | 10 | 1 | 1 |
| 86 | 0.0 | 11.5 | 0.0 | 5 | norm. | 1 | 1 | 1 | 1 | 1 |
| 86 | 0 | 3.8 | 0 | 5 | norm. | 12 | 1 | 1 | 1 | 1 |
| 86 | 0 | 2.0 | 0 | 5 | norm. | 21 | 1 | 1 | 1 | 1 |
| 89 | 0 | 2.0 | 0 | 5 | norm. | 16 | 1 | 1 | 1 | 1 |
| 89 | 0 | 5.8 | 0 | 14 | norm. | 22 | 1 | 1 | 1 | 4 |
| 89 | 0 | 5.0 | 0 | 6 | norm. | 21 | 1 | 1 | 1 | 1 |

TABLE A-continued

| | | | | | | | | | |
|---|---|---|---|---|---|---|---|---|---|
| 91 | 0 | 0.2 | 0 | 16 | norm. | 46 | 1 | 5 | 1 | 4 |
| 91 | 0 | 0.3 | 0 | 17 | norm. | 61 | 1 | 5 | 1 | 4 |
| 91 | 0 | 0.2 | 0 | 25 | norm. | 46 | 1 | 5 | 1 | 4 |
| 105 | 0.0 | 2.6 | 0.0 | 8.7 | norm. | 30 | 1 | 1 | 1 | 1 |
| 105 | 0 | 2.5 | 0 | 5.1 | norm. | 27 | 1 | 1 | 1 | 1 |
| 105 | 0 | 2.6 | 0 | 7.9 | norm. | 27 | 1 | 1 | 1 | 1 |
| 115 | 0 | 2.4 | 66 | 5 | norm. | 7 | 1 | 1 | 4 | 1 |
| 115 | 0 | 2.1 | 0 | 6 | norm. | 5 | 1 | 1 | 1 | 1 |
| 116 | 0 | 0.0 | 0 | 12.7 | norm. | 46 | 1 | 10 | 1 | 4 |
| 116 | 11 | 18.9 | 0 | 5 | norm. | 31 | 4 | 1 | 1 | 1 |
| 116 | 0 | 5.9 | 0 | 5 | norm. | 57 | 1 | 1 | 1 | 1 |
| 117 | 0 | 0.9 | 0 | 5 | norm. | 22 | 1 | 3 | 1 | 1 |
| 117 | 0 | 3.2 | 0 | 24 | norm. | 41 | 1 | 1 | 1 | 4 |
| 117 | 0 | 2.1 | 0 | 5 | norm. | 18 | 1 | 1 | 1 | 1 |
| 119 | 0 | 2.3 | 0 | 5 | norm. | 29 | 1 | 1 | 1 | 1 |
| 119 | 0 | 1.5 | 11 | 5 | norm. | 40 | 1 | 3 | 4 | 1 |
| 129 | 0 | 4.1 | 0 | 5 | norm. | 8 | 1 | 1 | 1 | 1 |
| 129 | 0 | 3.9 | 0 | 5 | norm. | 2 | 1 | 1 | 1 | 1 |
| 129 | 0 | 4.3 | 0 | 5 | norm. | 3 | 1 | 1 | 1 | 1 |
| 138 | 0 | 0.0 | 0 | 14 | norm. | 28 | 1 | 10 | 1 | 4 |
| 138 | 0 | 12.4 | 0 | 5 | norm. | 11 | 1 | 1 | 1 | 1 |
| 138 | 0 | 9.9 | 0 | 5 | norm. | 11 | 1 | 1 | 1 | 1 |
| 92 | 0 | 0.5 | 0 | 5 | norm. | 38 | 1 | 5 | 1 | 1 |
| 92 | 0 | 0.5 | 0 | 17 | norm. | 51 | 1 | 5 | 1 | 4 |
| 92 | 0 | 0.3 | 0 | 5 | norm. | 25 | 1 | 5 | 1 | 1 |

| Patient | scoring factors | | weighting factors | | | | | SCORING | Treatment Response |
|---|---|---|---|---|---|---|---|---|---|
| | VS | posology | TNF | Infliximab | ADA | CRP | VS | | |
| 7 | 1 | 1 | 0.15 | 0.3 | 0.35 | 0.1 | 0.1 | 3.7 | T0 |
| 7 | 1 | 1 | 0.15 | 0.3 | 0.35 | 0.1 | 0.1 | 1.0 | R |
| 7 | 1 | 1 | 0.15 | 0.3 | 0.35 | 0.1 | 0.1 | 1.6 | R |
| 20 | 1 | 1 | 0.15 | 0.3 | 0.35 | 0.1 | 0.1 | 4.8 | NR |
| 20 | 4 | 1 | 0.15 | 0.3 | 0.35 | 0.1 | 0.1 | 7.2 | NR |
| 20 | 10 | 1 | 0.15 | 0.3 | 0.35 | 0.1 | 0.1 | 5.7 | NR |
| 20 | 4 | 1 | 0.15 | 0.3 | 0.35 | 0.1 | 0.1 | 5.1 | NR |
| 21 | 10 | 1 | 0.15 | 0.3 | 0.35 | 0.1 | 0.1 | 4.6 | T0 |
| 21 | 10 | 1 | 0.15 | 0.3 | 0.35 | 0.1 | 0.1 | 1.9 | R |
| 21 | 10 | 1 | 0.15 | 0.3 | 0.35 | 0.1 | 0.1 | 1.9 | R |
| 21 | 10 | 1 | 0.15 | 0.3 | 0.35 | 0.1 | 0.1 | 1.9 | R |
| 31 | 1 | 1 | 0.15 | 0.3 | 0.35 | 0.1 | 0.1 | 1.0 | R |
| 31 | 1 | 1 | 0.15 | 0.3 | 0.35 | 0.1 | 0.1 | 1.0 | R |
| 31 | 10 | 1 | 0.15 | 0.3 | 0.35 | 0.1 | 0.1 | 6.0 | NR |
| 47 | 1 | 1 | 0.15 | 0.3 | 0.35 | 0.1 | 0.1 | 1.0 | R |
| 47 | 1 | 1 | 0.15 | 0.3 | 0.35 | 0.1 | 0.1 | 1.0 | R |
| 47 | 1 | 1 | 0.15 | 0.3 | 0.35 | 0.1 | 0.1 | 1.0 | R |
| 47 | 1 | 1 | 0.15 | 0.3 | 0.35 | 0.1 | 0.1 | 1.0 | R |
| 49 | 10 | 1.3 | 0.15 | 0.3 | 0.35 | 0.1 | 0.1 | 2.3 | R |
| 49 | 1 | 1.3 | 0.15 | 0.3 | 0.35 | 0.1 | 0.1 | 1.1 | R |
| 49 | 10 | 1.3 | 0.15 | 0.3 | 0.35 | 0.1 | 0.1 | 5.7 | NR |
| 58 | 1 | 1 | 0.15 | 0.3 | 0.35 | 0.1 | 0.1 | 1.0 | R |
| 58 | 1 | 1 | 0.15 | 0.3 | 0.35 | 0.1 | 0.1 | 1.6 | R |
| 58 | 1 | 1 | 0.15 | 0.3 | 0.35 | 0.1 | 0.1 | 1.0 | R |
| 67 | 10 | 1 | 0.15 | 0.3 | 0.35 | 0.1 | 0.1 | 6.4 | NR |
| 67 | 1 | 1 | 0.15 | 0.3 | 0.35 | 0.1 | 0.1 | 1.5 | R |
| 67 | 1 | 1 | 0.15 | 0.3 | 0.35 | 0.1 | 0.1 | 1.5 | R |
| 67 | 1 | 1 | 0.15 | 0.3 | 0.35 | 0.1 | 0.1 | 1.0 | R |
| 86 | 1 | 1 | 0.15 | 0.3 | 0.35 | 0.1 | 0.1 | 3.7 | T0 |
| 86 | 1 | 1 | 0.15 | 0.3 | 0.35 | 0.1 | 0.1 | 1.0 | R |
| 86 | 1 | 1 | 0.15 | 0.3 | 0.35 | 0.1 | 0.1 | 1.0 | R |
| 86 | 10 | 1 | 0.15 | 0.3 | 0.35 | 0.1 | 0.1 | 1.9 | R |
| 89 | 4 | 1 | 0.15 | 0.3 | 0.35 | 0.1 | 0.1 | 1.3 | NR |
| 89 | 10 | 1 | 0.15 | 0.3 | 0.35 | 0.1 | 0.1 | 2.2 | NR |
| 89 | 10 | 1 | 0.15 | 0.3 | 0.35 | 0.1 | 0.1 | 1.9 | NR |
| 91 | 10 | 1 | 0.15 | 0.3 | 0.35 | 0.1 | 0.1 | 3.4 | NR |
| 91 | 10 | 1 | 0.15 | 0.3 | 0.35 | 0.1 | 0.1 | 3.4 | NR |
| 91 | 10 | 1 | 0.15 | 0.3 | 0.35 | 0.1 | 0.1 | 3.4 | NR |
| 105 | 10 | 1 | 0.15 | 0.3 | 0.35 | 0.1 | 0.1 | 1.9 | R |
| 105 | 10 | 1 | 0.15 | 0.3 | 0.35 | 0.1 | 0.1 | 1.9 | R |
| 105 | 10 | 1 | 0.15 | 0.3 | 0.35 | 0.1 | 0.1 | 1.9 | R |
| 115 | 1 | 1 | 0.15 | 0.3 | 0.35 | 0.1 | 0.1 | 2.1 | R |
| 115 | 1 | 1 | 0.15 | 0.3 | 0.35 | 0.1 | 0.1 | 1.0 | R |
| 116 | 10 | 1 | 0.15 | 0.3 | 0.35 | 0.1 | 0.1 | 4.9 | T0 |
| 116 | 10 | 1 | 0.15 | 0.3 | 0.35 | 0.1 | 0.1 | 2.4 | R |
| 116 | 10 | 1 | 0.15 | 0.3 | 0.35 | 0.1 | 0.1 | 1.9 | R |
| 117 | 10 | 1 | 0.15 | 0.3 | 0.35 | 0.1 | 0.1 | 2.5 | R |
| 117 | 10 | 1 | 0.15 | 0.3 | 0.35 | 0.1 | 0.1 | 2.2 | R |
| 117 | 4 | 1 | 0.15 | 0.3 | 0.35 | 0.1 | 0.1 | 1.3 | R |
| 119 | 10 | 1 | 0.15 | 0.3 | 0.35 | 0.1 | 0.1 | 1.9 | R |

TABLE A-continued

| 119 | 10 | 1 | 0.15 | 0.3 | 0.35 | 0.1 | 0.1 | 3.6 | R |
|---|---|---|---|---|---|---|---|---|---|
| 129 | 1 | 1 | 0.15 | 0.3 | 0.35 | 0.1 | 0.1 | 1.0 | R |
| 129 | 1 | 1 | 0.15 | 0.3 | 0.35 | 0.1 | 0.1 | 1.0 | R |
| 129 | 1 | 1 | 0.15 | 0.3 | 0.35 | 0.1 | 0.1 | 1.0 | R |
| 138 | 10 | 1 | 0.15 | 0.3 | 0.35 | 0.1 | 0.1 | 4.9 | T0 |
| 138 | 1 | 1 | 0.15 | 0.3 | 0.35 | 0.1 | 0.1 | 1.0 | R |
| 138 | 1 | 1 | 0.15 | 0.3 | 0.35 | 0.1 | 0.1 | 1.0 | R |
| 92 | 10 | 1 | 0.15 | 0.3 | 0.35 | 0.1 | 0.1 | 3.1 | NR |
| 92 | 10 | 1 | 0.15 | 0.3 | 0.35 | 0.1 | 0.1 | 3.4 | NR |
| 92 | 10 | 1 | 0.15 | 0.3 | 0.35 | 0.1 | 0.1 | 3.1 | R |

The results presented in the above table A show that patients which combine (i) low or no detectable TNFalpha, (ii) detectable anti-TNF levels, and (iii) essentially low or no ADA level do respond to the treatment. Using the above scoring and weighting factors, patients with a score below 3 can be classified as responders. For such patients, the treatment may be continued (although dosage may be adjusted).

All patients having a scoring value above 5 should be classified as "escapers", i.e., patients in which anti-TNF treatment was effective but which have become non-responders. In these patients, the treatment should be switched rapidly to avoid irreversible degradation of the joints.

Patients between 3-5 should be monitored carefully. These patients are progressively becoming non-responders. The treatment should be adjusted (e.g., dosage or timing of administration), and possible switch should be considered depending on the progression.

1 patient only (patient #89) with a score below 3 was a non-responder. In fact, this patient is a primary non-responder, i.e., a patient in whom anti-TNF treatment was never effective. Such patients can be easily identified using the invention: they have a scoring similar to responders, but they have all clinical signs of sick patients. Their treatment should be changed.

7.2. Analysis of Patients with Inflammatory Diseases Treated with Infliximab

We also tested serum samples from Inflammatory diseases (Ankylosing Spondilytis, Crohn's disease, Psoriasis, etc.). The patients were treated with Infliximab. Samples were analyzed at different times during the course of the treatment. The figures in Table B below show, for each patient:
- the measured level of: TNF, anti-TNF (Infliximab), and ADA (anti-infliximab).
- the information from the clinical data set: CRP, ESR and posology,
- the scoring factor for each parameter
- the weighting factor r each parameter.
- the result of the score of monitoring
- the patient response to the treatment according to the whole clinical data set: response (R), no-response or incomplete response (NR), beginning of treatment (T0).

Consecutive results for each patient represent measures at different points during treatment.

TABLE B

| | Measured level of: | | | clinical data set | | | scoring factors | | | |
|---|---|---|---|---|---|---|---|---|---|---|
| patient | TNF | Infliximab | ADA | CRP | posology | VS | TNF | Infliximab | ADA | CRP |
| 1 | 0 | 0.00 | 0 | 17 | norm. | 35 | 1 | 10 | 1 | 4 |
| 1 | 0 | 21.3 | 0 | 5 | norm. | 16 | 1 | 1 | 1 | 1 |
| 1 | 0 | 26.6 | 0 | 5 | norm. | 13 | 1 | 1 | 1 | 1 |
| 2 | 0 | 1.0 | 0 | 5 | norm. | 4 | 1 | 3 | 1 | 1 |
| 2 | 0.0 | 0.8 | 0.0 | 5 | norm. | 1 | 1 | 3 | 1 | 1 |
| 3 | 0 | 1.0 | 0 | 11 | norm. | 40 | 1 | 3 | 1 | 4 |
| 3 | 0.0 | 1.6 | 0.0 | 5 | norm. | | 1 | 3 | 1 | 1 |
| 3 | 0 | 1.3 | 0 | 11 | norm. | 27 | 1 | 3 | 1 | 4 |
| 4 | 0 | 2.5 | 0 | 5 | norm. | 10 | 1 | 1 | 1 | 1 |
| 4 | 0.0 | 3.0 | 0.0 | 5 | norm. | 8 | 1 | 1 | 1 | 1 |
| 4 | 0 | 3.2 | 0 | 5 | norm. | 10 | 1 | 1 | 1 | 1 |
| 11 | 0 | 1.9 | 0 | 5 | norm. | 5 | 1 | 1 | 1 | 1 |
| 11 | 0.0 | 1.7 | 0.0 | 5 | norm. | 3 | 1 | 3 | 1 | 1 |
| 11 | 0 | 1.7 | 0 | 5 | norm. | 5 | 1 | 3 | 1 | 1 |
| 13 | 0 | 0.00 | 1250 | 5 | norm. | 1 | 1 | 10 | 10 | 1 |
| 13 | 14 | 0.0 | 1660 | 5 | norm. | 26 | 4 | 10 | 10 | 1 |
| 13 | 0 | 0.2 | 12 | 5 | norm. | 12 | 1 | 5 | 4 | 1 |
| 14 | 0 | 1.6 | 0 | 6.8 | norm. | 16 | 1 | 3 | 1 | 1 |
| 14 | 0 | 3.2 | 0 | 5 | norm. | 6 | 1 | 1 | 1 | 1 |
| 15 | 0 | 0.2 | 0 | 5 | norm. | 31 | 1 | 5 | 1 | 1 |
| 15 | 0 | 1.0 | 0 | 7 | high | 36 | 1 | 3 | 1 | 1 |
| 15 | 0 | 1.6 | 0 | 5 | high | 20 | 1 | 3 | 1 | 1 |
| 16 | 0 | 4.0 | 0 | 5 | high | 41 | 1 | 1 | 1 | 1 |
| 18 | 0 | 2.6 | 0 | 5 | norm. | 7 | 1 | 1 | 1 | 1 |
| 18 | 0 | 2.5 | 0 | 5 | norm. | 8 | 1 | 1 | 1 | 1 |
| 19 | 0 | 14.7 | 0 | 5 | norm. | 1 | 1 | 1 | 1 | 1 |
| 19 | 0.0 | 18.3 | 0.0 | 5 | norm. | 12 | 1 | 1 | 1 | 1 |
| 22 | 0 | 6.8 | 0 | 5 | norm. | 21 | 1 | 1 | 1 | 1 |
| 22 | 0 | 5.4 | 0 | 5.8 | norm. | 1 | 1 | 1 | 1 | 1 |
| 22 | 0 | 2.1 | 0 | 5 | norm. | 18 | 1 | 1 | 1 | 1 |
| 23 | 0 | 13.8 | 0 | 5 | high | 2 | 1 | 1 | 1 | 1 |
| 23 | 0.0 | 11.1 | 0.0 | 5 | high | 10 | 1 | 1 | 1 | 1 |
| 23 | 0 | 9.1 | 0 | 5 | high | 12 | 1 | 1 | 1 | 1 |

TABLE B-continued

| | | | | | | | | | | |
|---|---|---|---|---|---|---|---|---|---|---|
| 24 | 0 | 2.8 | 0 | 5 | norm. | 9 | 1 | 1 | 1 | 1 |
| 24 | 0.0 | 4.0 | 0.0 | 5 | norm. | 12 | 1 | 1 | 1 | 1 |
| 24 | 0 | 7.0 | 0 | 5 | norm. | 5 | 1 | 1 | 1 | 1 |
| 24 | 0 | 8.2 | 0 | 5 | norm. | 7 | 1 | 1 | 1 | 1 |
| 25 | 0 | 0.3 | 0 | 5 | norm. | 22 | 1 | 5 | 1 | 1 |
| 26 | 0.0 | 9.7 | 0.0 | 5 | high | 1 | 1 | 1 | 1 | 1 |
| 26 | 0 | 10.8 | 0 | 5 | high | 9 | 1 | 1 | 1 | 1 |
| 27 | 0 | 3.3 | 0 | 10 | norm. | 24 | 1 | 1 | 1 | 4 |
| 27 | 0.0 | 3.0 | 0.0 | 9.8 | norm. | 22 | 1 | 1 | 1 | 4 |
| 27 | 0 | 3.8 | 0 | 9.5 | norm. | 16 | 1 | 1 | 1 | 4 |
| 28 | 0 | 1.6 | 0 | 17.6 | norm. | 6 | 1 | 3 | 1 | 4 |
| 28 | 145 | 2.3 | 0 | 5 | norm. | 5 | 10 | 1 | 1 | 1 |
| 29 | 0 | 1.3 | 0 | 5 | norm. | 17 | 1 | 3 | 1 | 1 |
| 29 | 0 | 1.2 | 0 | 5 | norm. | 14 | 1 | 3 | 1 | 1 |
| 29 | 0 | 0.8 | 0 | 5 | norm. | 14 | 1 | 3 | 1 | 1 |
| 32 | 0 | 1.6 | 0 | 8 | high | 17 | 1 | 3 | 1 | 1 |
| 32 | 0.0 | 1.2 | 0.0 | 5 | high | 19 | 1 | 3 | 1 | 1 |
| 32 | 0 | 2.1 | 0 | 7 | high | 15 | 1 | 1 | 1 | 1 |
| 33 | 0 | 18.2 | 0 | 5 | high | 8 | 1 | 1 | 1 | 1 |
| 33 | 12 | 16.2 | 0.0 | 5 | high | 14 | 4 | 1 | 1 | 1 |
| 33 | 10 | >6 | 0 | 5 | high | 6 | 4 | 1 | 1 | 1 |
| 34 | 0 | 0.0 | 0 | 7 | norm. | 22 | 1 | 10 | 1 | 1 |
| 34 | 0 | 19.3 | 0 | 5 | norm. | 5 | 1 | 1 | 1 | 1 |
| 34 | 0.0 | 3.0 | 0.0 | 5 | norm. | 5 | 1 | 1 | 1 | 1 |
| 34 | 0 | 0.1 | 0 | 5 | norm. | 5 | 1 | 5 | 1 | 1 |
| 35 | 0 | 4.9 | 0 | 5 | high | 38 | 1 | 1 | 1 | 1 |
| 35 | 0.0 | 4.9 | 0.0 | 5 | high | 1 | 1 | 1 | 1 | 1 |
| 35 | 0 | 5.4 | 0 | 5 | high | 23 | 1 | 1 | 1 | 1 |
| 36 | 0 | 0.0 | 0 | 17.2 | norm. | 1 | 1 | 10 | 1 | 4 |
| 36 | 21 | 31.3 | 0.0 | 5 | norm. | 5 | 4 | 1 | 1 | 1 |
| 36 | 0 | 9.2 | 0 | 6 | norm. | 8 | 1 | 1 | 1 | 1 |
| 36 | 0 | 6.1 | 0 | 5 | norm. | 6 | 1 | 1 | 1 | 1 |
| 37 | 0 | 3.7 | 0 | 5 | norm. | 4 | 1 | 1 | 1 | 1 |
| 37 | 0 | 3.4 | 0 | 5 | norm. | 4 | 1 | 1 | 1 | 1 |
| 37 | 0 | 3.6 | 0 | 5 | norm. | 9 | 1 | 1 | 1 | 1 |
| 38 | 0 | 3.3 | 0 | 5 | norm. | 5 | 1 | 1 | 1 | 1 |
| 38 | 0.0 | 2.5 | 0.0 | 5 | norm. | 5 | 1 | 1 | 1 | 1 |
| 38 | 0 | 2.8 | 0 | 5 | norm. | 7 | 1 | 1 | 1 | 1 |
| 39 | 0 | 0.7 | 0 | 5 | norm. | 2 | 1 | 3 | 1 | 1 |
| 39 | 0.0 | 0.9 | 0.0 | 5 | norm. | 4 | 1 | 3 | 1 | 1 |
| 39 | 0 | 1.0 | 0 | 5 | norm. | 3 | 1 | 3 | 1 | 1 |
| 40 | 0 | 2.5 | 0 | 9 | high | 56 | 1 | 1 | 1 | 1 |
| 40 | 0.0 | 2.6 | 0.0 | 5.7 | high | 12 | 1 | 1 | 1 | 1 |
| 40 | 0 | 3.3 | 0 | 6.2 | high | 7 | 1 | 1 | 1 | 1 |
| 41 | 0 | 2.8 | 0 | 65 | norm. | 76 | 1 | 1 | 1 | 10 |
| 41 | 0 | 0.4 | 0 | 105 | norm. | 110 | 1 | 5 | 1 | 10 |
| 41 | 0 | 0.4 | 0 | 112 | norm. | 96 | 1 | 5 | 1 | 10 |
| 42 | 0 | 1.0 | 0 | 5 | norm. | 10 | 1 | 3 | 1 | 1 |
| 42 | 0 | 3.1 | 0 | 5 | norm. | 5 | 1 | 1 | 1 | 1 |
| 43 | 0 | 0.6 | 0 | 9 | norm. | 7 | 1 | 3 | 1 | 1 |
| 43 | 0.0 | 2.1 | 0.0 | 6 | norm. | 6 | 1 | 1 | 1 | 1 |
| 43 | 0 | 0.0 | 0 | 14 | norm. | 16 | 1 | 10 | 1 | 4 |
| 44 | 0 | 6.0 | 0 | 5 | norm. | 3 | 1 | 1 | 1 | 1 |
| 44 | 0.0 | 2.6 | 0.0 | 5 | norm. | 1 | 1 | 1 | 1 | 1 |
| 44 | 0 | 2.8 | 0 | 3 | norm. | 2 | 1 | 1 | 1 | 1 |
| 45 | 0 | 7.8 | 0 | 5 | norm. | 5 | 1 | 1 | 1 | 1 |
| 45 | 0 | 2.5 | 0 | 5 | high | 8 | 1 | 1 | 1 | 1 |
| 45 | 0 | 5.2 | 0 | 5 | high | 6 | 1 | 1 | 1 | 1 |
| 45 | 0 | 4.4 | 0 | 6 | high | 7 | 1 | 1 | 1 | 1 |
| 46 | 0 | 0.0 | 610 | 5 | norm. | 8 | 1 | 10 | 10 | 1 |
| 46 | 12 | 0.0 | 848 | 5 | norm. | 5 | 4 | 10 | 10 | 1 |
| 46 | 0 | 0.0 | 895 | 5 | norm. | 9 | 1 | 10 | 10 | 1 |
| 48 | 0 | 1.3 | 0 | 5 | norm. | 7 | 1 | 3 | 1 | 1 |
| 48 | 0.0 | 2.9 | 0.0 | 5 | norm. | 1 | 1 | 1 | 1 | 1 |
| 48 | 0 | 0.4 | 0 | 19 | norm. | 49 | 1 | 5 | 1 | 4 |
| 50 | 0 | 1.3 | 0 | 5 | norm. | 4 | 1 | 3 | 1 | 1 |
| 50 | 0 | 0.6 | 12 | 5 | norm. | 3 | 1 | 3 | 10 | 1 |
| 50 | 0 | 1.6 | 0 | 5 | norm. | 1 | 1 | 3 | 1 | 1 |
| 51 | 0 | 0.0 | 117 | 11 | norm. | 9 | 1 | 10 | 4 | 4 |
| 51 | 0.0 | 0.0 | 0.0 | 8.1 | norm. | 8 | 1 | 10 | 1 | 1 |
| 51 | 0 | 0.5 | 0 | 5 | norm. | 10 | 1 | 5 | 1 | 1 |
| 52 | 19 | 0.0 | 0 | 12.5 | norm. | 17 | 4 | 10 | 1 | 4 |
| 52 | 0 | 7.0 | 0 | 5 | norm. | 6 | 1 | 1 | 1 | 1 |
| 52 | 0 | 2.0 | 0 | 5 | norm. | 11 | 1 | 1 | 1 | 1 |
| 52 | 0 | 0.3 | 0 | 13 | norm. | 12 | 1 | 5 | 1 | 4 |
| 52 | 0 | 0.1 | 0 | 9.6 | norm. | 14 | 1 | 5 | 1 | 4 |
| 56 | 0 | 7.2 | 0 | 5 | high | 1 | 1 | 1 | 1 | 1 |
| 56 | 12 | 12.0 | 0.0 | 5 | high | 2 | 4 | 1 | 1 | 1 |
| 56 | 0 | 6.5 | 0 | 5 | high | 2 | 1 | 1 | 1 | 1 |
| 59 | 0 | 3.9 | 0 | 12.7 | norm. | 11 | 1 | 1 | 1 | 4 |

TABLE B-continued

| 59 | 0 | >3 | 0 | 5 | norm. | 18 | 10 | 1 | 1 | 1 |
|---|---|---|---|---|---|---|---|---|---|---|
| 59 | 0 | 4.2 | 0 | 5 | norm. | 20 | 1 | 1 | 1 | 1 |
| 60 | 0.0 | 0.0 | 0.0 | 5 | norm. | 8 | 1 | 10 | 1 | 1 |
| 60 | 0.0 | 23.2 | 0.0 | 5 | norm. | 8 | 1 | 1 | 1 | 1 |
| 68 | 0 | 0.0 | 0 | 5 | norm. | 1 | 1 | 10 | 1 | 1 |
| 68 | 0 | 3.2 | 0 | 5 | norm. | 9 | 1 | 1 | 1 | 1 |
| 68 | 0 | 5.5 | 0 | 5 | norm. | 13 | 1 | 1 | 1 | 1 |
| 69 | 0 | 0.0 | 0 | 5.1 | norm. | 10 | 1 | 10 | 1 | 1 |
| 69 | 0.0 | 0.0 | 10 | 5 | norm. | 12 | 1 | 10 | 4 | 1 |
| 69 | 0 | 0.0 | 607 | 5 | norm. | 17 | 1 | 10 | 10 | 1 |
| 69 | 0 | 0.0 | 174 | 5 | norm. | 19 | 1 | 10 | 4 | 1 |
| 70 | 0 | 10.4 | 0 | 5 | high | 1 | 1 | 1 | 1 | 1 |
| 70 | 0.0 | 9.4 | 0.0 | 5 | high | 1 | 1 | 1 | 1 | 1 |
| 71 | 0 | 0.3 | 0 | 6.3 | high | 49 | 1 | 5 | 1 | 1 |
| 71 | 0 | 0.8 | 0 | 11 | high | 46 | 1 | 3 | 1 | 4 |
| 72 | 0 | 0.0 | 0 |  |  | 1 | 1 | 10 | 1 | 1 |
| 72 | 22 | 0.0 | 930 | 59.6 | norm. | 63 | 4 | 10 | 10 | 10 |
| 72 | 10 | 0.0 | 8652 | 59 | norm. | 68 | 4 | 10 | 10 | 10 |
| 72 | 24 | 0.0 | 23831 | 63 | norm. | 80 | 4 | 10 | 10 | 10 |
| 73 | 1092 | 0.0 | 80522 | 5 | norm. | 58 | 10 | 10 | 10 | 1 |
| 73 | 995 | 0.0 | 191144 | 5 | norm. | 38 | 10 | 10 | 10 | 1 |
| 73 | 896 | 0.1 | #### | 5 | norm. | 60 | 10 | 5 | 10 | 1 |
| 73 | 488 | 0.0 | 95835 | 7.7 | norm. | 58 | 10 | 10 | 10 | 1 |
| 73 | 462 | 0.0 | 148001 | 8 | norm. | 64 | 10 | 10 | 10 | 1 |
| 75 | 0 | 0.6 | 0 | 5 | norm. | 8 | 1 | 3 | 1 | 1 |
| 75 | 0 | 1.5 | 0 | 5 | norm. |  | 1 | 3 | 1 | 1 |
| 75 | 0 | 3.2 | 0 | 5 | norm. | 23 | 1 | 1 | 1 | 1 |
| 76 | 0 | 7.8 | 0 | 3 | high | 9 | 1 | 1 | 1 | 1 |
| 77 | 0 | 9.2 | 0 | 5 | norm. | 10 | 1 | 1 | 1 | 1 |
| 77 | 0 | 2.8 | 0 | 5 | norm. | 15 | 1 | 1 | 1 | 1 |
| 78 | 0 | 4.8 | 0 | 12 | high | 19 | 1 | 1 | 1 | 4 |
| 78 | 0 | 8.1 | 0 | 10.8 | high | 20 | 1 | 1 | 1 | 4 |
| 78 | 0 | 6.1 | 0 | 6.7 | high | 21 | 1 | 1 | 1 | 1 |
| 79 | 0 | 1.8 | 0 | 5 | norm. | 4 | 1 | 3 | 1 | 1 |
| 80 | 0 | 3.2 | 0 | 5.6 | high | 3 | 1 | 1 | 1 | 1 |
| 80 | 11 | 5.0 | 0 | 5 | high | 3 | 4 | 1 | 1 | 1 |
| 80 | 0 | 4.8 | 0 | 5 | high | 3 | 1 | 1 | 1 | 1 |
| 80 | 0 | 2.8 | 0 | 5 | high | 3 | 1 | 1 | 1 | 1 |
| 81 | 10 | 17.2 | 0 | 5 | high | 8 | 4 | 1 | 1 | 1 |
| 81 | 20 | 18.8 | 0 | 5 | high | 6 | 4 | 1 | 1 | 1 |
| 81 | 15 | 11.0 | 0 | 5 | high | 12 | 4 | 1 | 1 | 1 |
| 82 | 25 | 22.3 | 0 | 20 | norm. | 22 | 4 | 1 | 1 | 4 |
| 82 | 24 | 18.4 | 0 | 36.4 | norm. | 22 | 4 | 1 | 1 | 4 |
| 82 | 0 | 5.3 | 0 | 99.2 | norm. | 24 | 1 | 1 | 1 | 10 |
| 83 | 0 | 3.6 | 0 | 12 | norm. | 7 | 1 | 1 | 1 | 4 |
| 83 | 0 | 4.8 | 0 | 18 | norm. | 8 | 1 | 1 | 1 | 4 |
| 83 | 0 | 2.9 | 0 | 11 | norm. | 10 | 1 | 1 | 1 | 4 |
| 84 | 0 | 5.3 | 0 | 8 | norm. | 4 | 1 | 1 | 1 | 1 |
| 84 | 0 | 3.9 | 0 | 9 | norm. | 4 | 1 | 1 | 1 | 1 |
| 85 | 0 | 1.0 | 0 | 5 | norm. | 14 | 1 | 3 | 1 | 1 |
| 85 | 0 | 0.8 | 0 | 5 | norm. | 9 | 1 | 3 | 1 | 1 |
| 85 | 0 | 0.4 | 0 | 5 | norm. | 3 | 1 | 5 | 1 | 1 |
| 87 | 0 | 0.8 | 0 | 5 | norm. | 6 | 1 | 3 | 1 | 1 |
| 87 | 0 | 1.0 | 0 | 5 | norm. | 20 | 1 | 3 | 1 | 1 |
| 93 | 0 | 2.4 | 0 | 18 | norm. | 69.7 | 1 | 1 | 1 | 4 |
| 93 | 0 | 1.9 | 0 | 22 | norm. | 29 | 1 | 1 | 1 | 4 |
| 93 | 0 | 2.0 | 0 | 16 | norm. | 12 | 1 | 1 | 1 | 4 |
| 95 | 0 | 3.1 | 0 | 25 | norm. | 8.3 | 1 | 1 | 1 | 4 |
| 95 | 0 | 3.7 | 0 | 5 | norm. | 7 | 1 | 1 | 1 | 1 |
| 97 | 0.0 | 4.7 | 0.0 | 5 | norm. | 3 | 1 | 1 | 1 | 1 |
| 97 | 0 | 13.3 | 0 | 5 | high | 3 | 1 | 1 | 1 | 1 |
| 97 | 0 | 10.8 | 0 | 5 | high | 1 | 1 | 1 | 1 | 1 |
| 99 | 27 | 13.9 | 0 | 5 | high | 12 | 4 | 1 | 1 | 1 |
| 102 | 0.0 | 1.0 | 0.0 | 7.8 | norm. | 18 | 1 | 3 | 1 | 1 |
| 102 | 0 | 1.4 | 0 | 5 | norm. | 20 | 1 | 3 | 1 | 1 |
| 102 | 0 | 0.5 | 0 | 5 | norm. | 21 | 1 | 5 | 1 | 1 |
| 104 | 0.0 | 1.9 | 0.0 | 5 | norm. | 5 | 1 | 1 | 1 | 1 |
| 104 | 0 | 1.9 | 0 | 5 | norm. | 5 | 1 | 1 | 1 | 1 |
| 104 | 0 | 1.7 | 0 | 5 | norm. | 6 | 1 | 3 | 1 | 1 |
| 108 | 0 | 0.6 | 0 | 5 | norm. | 4 | 1 | 3 | 1 | 1 |
| 120 | 0.0 | 0.0 | 0.0 | 103 | norm. | 76 | 1 | 10 | 1 | 10 |
| 120 | 18 | 13.8 | 0 | 72.2 | norm. | 57 | 4 | 1 | 1 | 10 |
| 120 | 0 | 2.2 | 0 | 72.2 | norm. | 57 | 1 | 1 | 1 | 10 |
| 120 | 0 | 0.1 | 0 | 39 | norm. | 59 | 1 | 5 | 1 | 4 |
| 122 | 197 | 0.0 | 711 | 6 | norm. | 13 | 10 | 10 | 10 | 1 |
| 122 | 62 | 0.0 | 84265 | 5 | norm. | 14 | 4 | 10 | 10 | 1 |
| 122 | 32 | 0.0 | 39638 | 6 | norm. | 18 | 4 | 10 | 10 | 1 |
| 123 | 0 | 0.0 | 0 | 28.7 | norm. | 15 | 1 | 10 | 1 | 4 |
| 123 | 15 | 18.7 | 0 | 6 | norm. | 16 | 4 | 1 | 1 | 1 |
| 123 | 0 | 0.0 | 23 | 6 | norm. | 16 | 1 | 10 | 4 | 1 |

TABLE B-continued

| | | | | | | | | | |
|---|---|---|---|---|---|---|---|---|---|
| 123 | 0 | 6.7 | 0 | 6 | norm. | 16 | 1 | 1 | 1 | 1 |
| 123 | 0 | 0.0 | 2075 | 24 | norm. | 30 | 1 | 10 | 10 | 4 |
| 124 | 10 | 17.5 | 0 | 5 | norm. | 4 | 4 | 1 | 1 | 1 |
| 124 | 0 | 8.4 | 0 | 5 | norm. | 8 | 1 | 1 | 1 | 1 |
| 156 | 27 | 0.0 | 0 | 10.4 | norm. | 32 | 4 | 10 | 1 | 4 |
| 156 | 20 | 16.1 | 0 | 5 | norm. | 35 | 4 | 1 | 1 | 1 |
| 156 | 0 | 9.7 | 0 | 9 | norm. | 53 | 1 | 1 | 1 | 1 |
| 158 | 0 | 0.2 | 0 | 5 | norm. | 25 | 1 | 5 | 1 | 1 |

| | scoring factors | | weighting factors | | | | | | Treatment |
|---|---|---|---|---|---|---|---|---|---|
| patient | VS | posology | TNF | Infliximab | ADA | CRP | VS | SCORING | response |
| 1 | 10 | 1 | 0.15 | 0.3 | 0.35 | 0.1 | 0.1 | 4.9 | T0 |
| 1 | 4 | 1 | 0.15 | 0.3 | 0.35 | 0.1 | 0.1 | 1.3 | R |
| 1 | 1 | 1 | 0.15 | 0.3 | 0.35 | 0.1 | 0.1 | 1.0 | R |
| 2 | 1 | 1 | 0.15 | 0.3 | 0.35 | 0.1 | 0.1 | 1.6 | R |
| 2 | 1 | 1 | 0.15 | 0.3 | 0.35 | 0.1 | 0.1 | 1.6 | R |
| 3 | 10 | 1 | 0.15 | 0.3 | 0.35 | 0.1 | 0.1 | 2.8 | R |
| 3 | 1 | 1 | 0.15 | 0.3 | 0.35 | 0.1 | 0.1 | 1.6 | R |
| 3 | 10 | 1 | 0.15 | 0.3 | 0.35 | 0.1 | 0.1 | 2.8 | R |
| 4 | 1 | 1 | 0.15 | 0.3 | 0.35 | 0.1 | 0.1 | 1.0 | R |
| 4 | 1 | 1 | 0.15 | 0.3 | 0.35 | 0.1 | 0.1 | 1.0 | R |
| 4 | 1 | 1 | 0.15 | 0.3 | 0.35 | 0.1 | 0.1 | 1.0 | R |
| 11 | 1 | 1 | 0.15 | 0.3 | 0.35 | 0.1 | 0.1 | 1.0 | R |
| 11 | 1 | 1 | 0.15 | 0.3 | 0.35 | 0.1 | 0.1 | 1.6 | R |
| 11 | 1 | 1 | 0.15 | 0.3 | 0.35 | 0.1 | 0.1 | 1.6 | R |
| 13 | 1 | 1 | 0.15 | 0.3 | 0.35 | 0.1 | 0.1 | 6.9 | NR |
| 13 | 10 | 1 | 0.15 | 0.3 | 0.35 | 0.1 | 0.1 | 8.2 | NR |
| 13 | 1 | 1 | 0.15 | 0.3 | 0.35 | 0.1 | 0.1 | 3.3 | NR |
| 14 | 4 | 1 | 0.15 | 0.3 | 0.35 | 0.1 | 0.1 | 1.9 | R |
| 14 | 1 | 1 | 0.15 | 0.3 | 0.35 | 0.1 | 0.1 | 1.0 | R |
| 15 | 10 | 1 | 0.15 | 0.3 | 0.35 | 0.1 | 0.1 | 3.1 | NR |
| 15 | 10 | 1.25 | 0.15 | 0.3 | 0.35 | 0.1 | 0.1 | 2.7 | R |
| 15 | 4 | 1.25 | 0.15 | 0.3 | 0.35 | 0.1 | 0.1 | 2.1 | R |
| 16 | 10 | 1.25 | 0.15 | 0.3 | 0.35 | 0.1 | 0.1 | 2.0 | R |
| 18 | 1 | 1 | 0.15 | 0.3 | 0.35 | 0.1 | 0.1 | 1.0 | R |
| 18 | 1 | 1 | 0.15 | 0.3 | 0.35 | 0.1 | 0.1 | 1.0 | R |
| 19 | 1 | 1 | 0.15 | 0.3 | 0.35 | 0.1 | 0.1 | 1.0 | R |
| 19 | 1 | 1 | 0.15 | 0.3 | 0.35 | 0.1 | 0.1 | 1.0 | R |
| 22 | 10 | 1 | 0.15 | 0.3 | 0.35 | 0.1 | 0.1 | 1.9 | R |
| 22 | 1 | 1 | 0.15 | 0.3 | 0.35 | 0.1 | 0.1 | 1.0 | R |
| 22 | 4 | 1 | 0.15 | 0.3 | 0.35 | 0.1 | 0.1 | 1.3 | R |
| 23 | 1 | 1.25 | 0.15 | 0.3 | 0.35 | 0.1 | 0.1 | 1.1 | R |
| 23 | 1 | 1.25 | 0.15 | 0.3 | 0.35 | 0.1 | 0.1 | 1.1 | R |
| 23 | 1 | 1.25 | 0.15 | 0.3 | 0.35 | 0.1 | 0.1 | 1.1 | R |
| 24 | 1 | 1 | 0.15 | 0.3 | 0.35 | 0.1 | 0.1 | 1.0 | NR |
| 24 | 1 | 1 | 0.15 | 0.3 | 0.35 | 0.1 | 0.1 | 1.0 | NR |
| 24 | 1 | 1 | 0.15 | 0.3 | 0.35 | 0.1 | 0.1 | 1.0 | NR |
| 24 | 1 | 1 | 0.15 | 0.3 | 0.35 | 0.1 | 0.1 | 1.0 | R |
| 25 | 10 | 1 | 0.15 | 0.3 | 0.35 | 0.1 | 0.1 | 3.1 | NR |
| 26 | 1 | 1.25 | 0.15 | 0.3 | 0.35 | 0.1 | 0.1 | 1.1 | R |
| 26 | 1 | 1.25 | 0.15 | 0.3 | 0.35 | 0.1 | 0.1 | 1.1 | R |
| 27 | 10 | 1 | 0.15 | 0.3 | 0.35 | 0.1 | 0.1 | 2.2 | R |
| 27 | 10 | 1 | 0.15 | 0.3 | 0.35 | 0.1 | 0.1 | 2.2 | R |
| 27 | 4 | 1 | 0.15 | 0.3 | 0.35 | 0.1 | 0.1 | 1.6 | R |
| 28 | 1 | 1 | 0.15 | 0.3 | 0.35 | 0.1 | 0.1 | 1.9 | R |
| 28 | 1 | 1 | 0.15 | 0.3 | 0.35 | 0.1 | 0.1 | 2.4 | R |
| 29 | 4 | 1 | 0.15 | 0.3 | 0.35 | 0.1 | 0.1 | 1.9 | R |
| 29 | 1 | 1 | 0.15 | 0.3 | 0.35 | 0.1 | 0.1 | 1.6 | R |
| 29 | 1 | 1 | 0.15 | 0.3 | 0.35 | 0.1 | 0.1 | 1.6 | R |
| 32 | 4 | 1.25 | 0.15 | 0.3 | 0.35 | 0.1 | 0.1 | 2.1 | NR |
| 32 | 4 | 1.25 | 0.15 | 0.3 | 0.35 | 0.1 | 0.1 | 2.1 | NR |
| 32 | 1 | 1.25 | 0.15 | 0.3 | 0.35 | 0.1 | 0.1 | 1.1 | NR |
| 33 | 1 | 1.25 | 0.15 | 0.3 | 0.35 | 0.1 | 0.1 | 1.1 | R |
| 33 | 1 | 1.25 | 0.15 | 0.3 | 0.35 | 0.1 | 0.1 | 1.5 | R |
| 33 | 1 | 1.25 | 0.15 | 0.3 | 0.35 | 0.1 | 0.1 | 1.5 | R |
| 34 | 10 | 1 | 0.15 | 0.3 | 0.35 | 0.1 | 0.1 | 4.6 | T0 |
| 34 | 1 | 1 | 0.15 | 0.3 | 0.35 | 0.1 | 0.1 | 1.0 | R |
| 34 | 1 | 1 | 0.15 | 0.3 | 0.35 | 0.1 | 0.1 | 1.0 | R |
| 34 | 1 | 1 | 0.15 | 0.3 | 0.35 | 0.1 | 0.1 | 2.2 | R |
| 35 | 10 | 1.25 | 0.15 | 0.3 | 0.35 | 0.1 | 0.1 | 2.0 | R |
| 35 | 1 | 1.25 | 0.15 | 0.3 | 0.35 | 0.1 | 0.1 | 1.1 | R |
| 35 | 10 | 1.25 | 0.15 | 0.3 | 0.35 | 0.1 | 0.1 | 2.0 | R |
| 36 | 1 | 1 | 0.15 | 0.3 | 0.35 | 0.1 | 0.1 | 4.0 | T0 |
| 36 | 1 | 1 | 0.15 | 0.3 | 0.35 | 0.1 | 0.1 | 1.5 | R |
| 36 | 1 | 1 | 0.15 | 0.3 | 0.35 | 0.1 | 0.1 | 1.0 | R |
| 36 | 1 | 1 | 0.15 | 0.3 | 0.35 | 0.1 | 0.1 | 1.0 | R |
| 37 | 1 | 1 | 0.15 | 0.3 | 0.35 | 0.1 | 0.1 | 1.0 | R |
| 37 | 1 | 1 | 0.15 | 0.3 | 0.35 | 0.1 | 0.1 | 1.0 | R |

TABLE B-continued

| | | | | | | | | | |
|---|---|---|---|---|---|---|---|---|---|
| 37 | 1 | 1 | 0.15 | 0.3 | 0.35 | 0.1 | 0.1 | 1.0 | R |
| 38 | 1 | 1 | 0.15 | 0.3 | 0.35 | 0.1 | 0.1 | 1.0 | R |
| 38 | 1 | 1 | 0.15 | 0.3 | 0.35 | 0.1 | 0.1 | 1.0 | R |
| 38 | 1 | 1 | 0.15 | 0.3 | 0.35 | 0.1 | 0.1 | 1.0 | R |
| 39 | 1 | 1 | 0.15 | 0.3 | 0.35 | 0.1 | 0.1 | 1.6 | R |
| 39 | 1 | 1 | 0.15 | 0.3 | 0.35 | 0.1 | 0.1 | 1.6 | R |
| 39 | 1 | 1 | 0.15 | 0.3 | 0.35 | 0.1 | 0.1 | 1.6 | R |
| 40 | 10 | 1.25 | 0.15 | 0.3 | 0.35 | 0.1 | 0.1 | 2.0 | NR |
| 40 | 1 | 1.25 | 0.15 | 0.3 | 0.35 | 0.1 | 0.1 | 1.1 | NR |
| 40 | 1 | 1.25 | 0.15 | 0.3 | 0.35 | 0.1 | 0.1 | 1.1 | NR |
| 41 | 10 | 1 | 0.15 | 0.3 | 0.35 | 0.1 | 0.1 | 2.8 | R |
| 41 | 10 | 1 | 0.15 | 0.3 | 0.35 | 0.1 | 0.1 | 4.0 | NR |
| 41 | 10 | 1 | 0.15 | 0.3 | 0.35 | 0.1 | 0.1 | 4.0 | NR |
| 42 | 1 | 1 | 0.15 | 0.3 | 0.35 | 0.1 | 0.1 | 1.6 | NR |
| 42 | 1 | 1 | 0.15 | 0.3 | 0.35 | 0.1 | 0.1 | 1.0 | R |
| 43 | 1 | 1 | 0.15 | 0.3 | 0.35 | 0.1 | 0.1 | 1.6 | R |
| 43 | 1 | 1 | 0.15 | 0.3 | 0.35 | 0.1 | 0.1 | 1.0 | R |
| 43 | 4 | 1 | 0.15 | 0.3 | 0.35 | 0.1 | 0.1 | 4.3 | NR |
| 44 | 1 | 1 | 0.15 | 0.3 | 0.35 | 0.1 | 0.1 | 1.0 | R |
| 44 | 1 | 1 | 0.15 | 0.3 | 0.35 | 0.1 | 0.1 | 1.0 | R |
| 44 | 1 | 1 | 0.15 | 0.3 | 0.35 | 0.1 | 0.1 | 1.0 | R |
| 45 | 1 | 1.25 | 0.15 | 0.3 | 0.35 | 0.1 | 0.1 | 1.1 | R |
| 45 | 1 | 1.25 | 0.15 | 0.3 | 0.35 | 0.1 | 0.1 | 1.1 | R |
| 45 | 1 | 1.25 | 0.15 | 0.3 | 0.35 | 0.1 | 0.1 | 1.1 | R |
| 45 | 1 | 1.25 | 0.15 | 0.3 | 0.35 | 0.1 | 0.1 | 1.1 | R |
| 46 | 1 | 1 | 0.15 | 0.3 | 0.35 | 0.1 | 0.1 | 6.9 | NR |
| 46 | 1 | 1 | 0.15 | 0.3 | 0.35 | 0.1 | 0.1 | 7.3 | NR |
| 46 | 1 | 1 | 0.15 | 0.3 | 0.35 | 0.1 | 0.1 | 6.9 | NR |
| 48 | 1 | 1.25 | 0.15 | 0.3 | 0.35 | 0.1 | 0.1 | 1.8 | R |
| 48 | 1 | 1.25 | 0.15 | 0.3 | 0.35 | 0.1 | 0.1 | 1.1 | R |
| 48 | 10 | 1.25 | 0.15 | 0.3 | 0.35 | 0.1 | 0.1 | 3.8 | NR |
| 50 | 1 | 1 | 0.15 | 0.3 | 0.35 | 0.1 | 0.1 | 1.6 | R |
| 50 | 1 | 1 | 0.15 | 0.3 | 0.35 | 0.1 | 0.1 | 4.8 | R |
| 50 | 1 | 1 | 0.15 | 0.3 | 0.35 | 0.1 | 0.1 | 1.6 | R |
| 51 | 1 | 1 | 0.15 | 0.3 | 0.35 | 0.1 | 0.1 | 5.1 | NR |
| 51 | 1 | 1 | 0.15 | 0.3 | 0.35 | 0.1 | 0.1 | 3.7 | NR |
| 51 | 1 | 1 | 0.15 | 0.3 | 0.35 | 0.1 | 0.1 | 2.2 | R |
| 52 | 4 | 1 | 0.15 | 0.3 | 0.35 | 0.1 | 0.1 | 4.8 | NR |
| 52 | 1 | 1 | 0.15 | 0.3 | 0.35 | 0.1 | 0.1 | 1.0 | R |
| 52 | 1 | 1 | 0.15 | 0.3 | 0.35 | 0.1 | 0.1 | 1.0 | NR |
| 52 | 1 | 1 | 0.15 | 0.3 | 0.35 | 0.1 | 0.1 | 2.5 | R |
| 52 | 1 | 1 | 0.15 | 0.3 | 0.35 | 0.1 | 0.1 | 2.5 | R |
| 56 | 1 | 1.25 | 0.15 | 0.3 | 0.35 | 0.1 | 0.1 | 1.1 | R |
| 56 | 1 | 1.25 | 0.15 | 0.3 | 0.35 | 0.1 | 0.1 | 1.5 | R |
| 56 | 1 | 1.25 | 0.15 | 0.3 | 0.35 | 0.1 | 0.1 | 1.1 | R |
| 59 | 1 | 1 | 0.15 | 0.3 | 0.35 | 0.1 | 0.1 | 1.3 | R |
| 59 | 4 | 1 | 0.15 | 0.3 | 0.35 | 0.1 | 0.1 | 2.7 | R |
| 59 | 4 | 1 | 0.15 | 0.3 | 0.35 | 0.1 | 0.1 | 1.3 | R |
| 60 | 1 | 1 | 0.15 | 0.3 | 0.35 | 0.1 | 0.1 | 3.7 | T0 |
| 60 | 1 | 1 | 0.15 | 0.3 | 0.35 | 0.1 | 0.1 | 1.0 | R |
| 68 | 1 | 1 | 0.15 | 0.3 | 0.35 | 0.1 | 0.1 | 3.7 | T0 |
| 68 | 1 | 1 | 0.15 | 0.3 | 0.35 | 0.1 | 0.1 | 1.0 | R |
| 68 | 1 | 1 | 0.15 | 0.3 | 0.35 | 0.1 | 0.1 | 1.0 | R |
| 69 | 1 | 1 | 0.15 | 0.3 | 0.35 | 0.1 | 0.1 | 3.7 | T0 |
| 69 | 1 | 1 | 0.15 | 0.3 | 0.35 | 0.1 | 0.1 | 4.8 | R |
| 69 | 4 | 1 | 0.15 | 0.3 | 0.35 | 0.1 | 0.1 | 7.2 | R |
| 69 | 4 | 1 | 0.15 | 0.3 | 0.35 | 0.1 | 0.1 | 5.1 | R |
| 70 | 1 | 1.25 | 0.15 | 0.3 | 0.35 | 0.1 | 0.1 | 1.1 | R |
| 70 | 1 | 1.25 | 0.15 | 0.3 | 0.35 | 0.1 | 0.1 | 1.1 | R |
| 71 | 10 | 1.25 | 0.15 | 0.3 | 0.35 | 0.1 | 0.1 | 3.5 | NR |
| 71 | 10 | 1.25 | 0.15 | 0.3 | 0.35 | 0.1 | 0.1 | 3.0 | NR |
| 72 | 1 | 1 | 0.15 | 0.3 | 0.35 | 0.1 | 0.1 | 3.7 | NR |
| 72 | 10 | 1 | 0.15 | 0.3 | 0.35 | 0.1 | 0.1 | 9.1 | NR |
| 72 | 10 | 1 | 0.15 | 0.3 | 0.35 | 0.1 | 0.1 | 9.1 | NR |
| 72 | 10 | 1 | 0.15 | 0.3 | 0.35 | 0.1 | 0.1 | 9.1 | NR |
| 73 | 10 | 1 | 0.15 | 0.3 | 0.35 | 0.1 | 0.1 | 9.1 | NR |
| 73 | 10 | 1 | 0.15 | 0.3 | 0.35 | 0.1 | 0.1 | 9.1 | NR |
| 73 | 10 | 1 | 0.15 | 0.3 | 0.35 | 0.1 | 0.1 | 7.6 | R |
| 73 | 10 | 1 | 0.15 | 0.3 | 0.35 | 0.1 | 0.1 | 9.1 | NR |
| 73 | 10 | 1 | 0.15 | 0.3 | 0.35 | 0.1 | 0.1 | 9.1 | R |
| 75 | 1 | 1 | 0.15 | 0.3 | 0.35 | 0.1 | 0.1 | 1.6 | R |
| 75 | 1 | 1 | 0.15 | 0.3 | 0.35 | 0.1 | 0.1 | 1.6 | R |
| 75 | 10 | 1 | 0.15 | 0.3 | 0.35 | 0.1 | 0.1 | 1.9 | R |
| 76 | 1 | 1.25 | 0.15 | 0.3 | 0.35 | 0.1 | 0.1 | 1.1 | R |
| 77 | 1 | 1 | 0.15 | 0.3 | 0.35 | 0.1 | 0.1 | 1.0 | R |
| 77 | 1 | 1 | 0.15 | 0.3 | 0.35 | 0.1 | 0.1 | 1.0 | R |
| 78 | 4 | 1.25 | 0.15 | 0.3 | 0.35 | 0.1 | 0.1 | 1.7 | R |
| 78 | 4 | 1.25 | 0.15 | 0.3 | 0.35 | 0.1 | 0.1 | 1.7 | R |
| 78 | 10 | 1.25 | 0.15 | 0.3 | 0.35 | 0.1 | 0.1 | 2.0 | R |
| 79 | 1 | 1 | 0.15 | 0.3 | 0.35 | 0.1 | 0.1 | 1.6 | R |

TABLE B-continued

| | | | | | | | | | |
|---|---|---|---|---|---|---|---|---|---|
| 80 | 1 | 1.25 | 0.15 | 0.3 | 0.35 | 0.1 | 0.1 | 1.1 | R |
| 80 | 1 | 1.25 | 0.15 | 0.3 | 0.35 | 0.1 | 0.1 | 1.5 | NR |
| 80 | 1 | 1.25 | 0.15 | 0.3 | 0.35 | 0.1 | 0.1 | 1.1 | NR |
| 80 | 1 | 1.25 | 0.15 | 0.3 | 0.35 | 0.1 | 0.1 | 1.1 | NR |
| 81 | 1 | 1.25 | 0.15 | 0.3 | 0.35 | 0.1 | 0.1 | 1.5 | R |
| 81 | 1 | 1.25 | 0.15 | 0.3 | 0.35 | 0.1 | 0.1 | 1.5 | R |
| 81 | 1 | 1.25 | 0.15 | 0.3 | 0.35 | 0.1 | 0.1 | 1.5 | R |
| 82 | 10 | 1 | 0.15 | 0.3 | 0.35 | 0.1 | 0.1 | 2.7 | R |
| 82 | 10 | 1 | 0.15 | 0.3 | 0.35 | 0.1 | 0.1 | 2.7 | R |
| 82 | 10 | 1 | 0.15 | 0.3 | 0.35 | 0.1 | 0.1 | 2.8 | R |
| 83 | 1 | 1 | 0.15 | 0.3 | 0.35 | 0.1 | 0.1 | 1.3 | R |
| 83 | 1 | 1 | 0.15 | 0.3 | 0.35 | 0.1 | 0.1 | 1.3 | R |
| 83 | 1 | 1 | 0.15 | 0.3 | 0.35 | 0.1 | 0.1 | 1.3 | R |
| 84 | 1 | 1 | 0.15 | 0.3 | 0.35 | 0.1 | 0.1 | 1.0 | R |
| 84 | 1 | 1 | 0.15 | 0.3 | 0.35 | 0.1 | 0.1 | 1.0 | R |
| 85 | 1 | 1 | 0.15 | 0.3 | 0.35 | 0.1 | 0.1 | 1.6 | R |
| 85 | 1 | 1 | 0.15 | 0.3 | 0.35 | 0.1 | 0.1 | 1.6 | R |
| 85 | 1 | 1 | 0.15 | 0.3 | 0.35 | 0.1 | 0.1 | 2.2 | R |
| 87 | 1 | 1 | 0.15 | 0.3 | 0.35 | 0.1 | 0.1 | 1.6 | R |
| 87 | 4 | 1 | 0.15 | 0.3 | 0.35 | 0.1 | 0.1 | 1.9 | R |
| 93 | 10 | 1 | 0.15 | 0.3 | 0.35 | 0.1 | 0.1 | 2.2 | R |
| 93 | 10 | 1 | 0.15 | 0.3 | 0.35 | 0.1 | 0.1 | 2.2 | R |
| 93 | 1 | 1 | 0.15 | 0.3 | 0.35 | 0.1 | 0.1 | 1.3 | R |
| 95 | 1 | 1 | 0.15 | 0.3 | 0.35 | 0.1 | 0.1 | 1.3 | R |
| 95 | 1 | 1 | 0.15 | 0.3 | 0.35 | 0.1 | 0.1 | 1.0 | R |
| 97 | 1 | 1 | 0.15 | 0.3 | 0.35 | 0.1 | 0.1 | 1.0 | R |
| 97 | 1 | 1.25 | 0.15 | 0.3 | 0.35 | 0.1 | 0.1 | 1.1 | R |
| 97 | 1 | 1.25 | 0.15 | 0.3 | 0.35 | 0.1 | 0.1 | 1.1 | R |
| 99 | 1 | 1.25 | 0.15 | 0.3 | 0.35 | 0.1 | 0.1 | 1.5 | R |
| 102 | 4 | 1 | 0.15 | 0.3 | 0.35 | 0.1 | 0.1 | 1.9 | R |
| 102 | 4 | 1 | 0.15 | 0.3 | 0.35 | 0.1 | 0.1 | 1.9 | R |
| 102 | 10 | 1 | 0.15 | 0.3 | 0.35 | 0.1 | 0.1 | 3.1 | R |
| 104 | 1 | 1 | 0.15 | 0.3 | 0.35 | 0.1 | 0.1 | 1.0 | R |
| 104 | 1 | 1 | 0.15 | 0.3 | 0.35 | 0.1 | 0.1 | 1.0 | R |
| 104 | 1 | 1 | 0.15 | 0.3 | 0.35 | 0.1 | 0.1 | 1.6 | R |
| 108 | 1 | 1 | 0.15 | 0.3 | 0.35 | 0.1 | 0.1 | 1.6 | R |
| 120 | 10 | 1 | 0.15 | 0.3 | 0.35 | 0.1 | 0.1 | 5.5 | T0 |
| 120 | 10 | 1 | 0.15 | 0.3 | 0.35 | 0.1 | 0.1 | 3.3 | R |
| 120 | 10 | 1 | 0.15 | 0.3 | 0.35 | 0.1 | 0.1 | 2.8 | NR |
| 120 | 10 | 1 | 0.15 | 0.3 | 0.35 | 0.1 | 0.1 | 3.4 | NR |
| 122 | 1 | 1 | 0.15 | 0.3 | 0.35 | 0.1 | 0.1 | 8.2 | NR |
| 122 | 1 | 1 | 0.15 | 0.3 | 0.35 | 0.1 | 0.1 | 7.3 | NR |
| 122 | 4 | 1 | 0.15 | 0.3 | 0.35 | 0.1 | 0.1 | 7.6 | NR |
| 123 | 1 | 1 | 0.15 | 0.3 | 0.35 | 0.1 | 0.1 | 4.0 | T0 |
| 123 | 4 | 1 | 0.15 | 0.3 | 0.35 | 0.1 | 0.1 | 1.8 | R |
| 123 | 4 | 1 | 0.15 | 0.3 | 0.35 | 0.1 | 0.1 | 5.1 | NR |
| 123 | 4 | 1 | 0.15 | 0.3 | 0.35 | 0.1 | 0.1 | 1.3 | R |
| 123 | 10 | 1 | 0.15 | 0.3 | 0.35 | 0.1 | 0.1 | 8.1 | NR |
| 124 | 1 | 1 | 0.15 | 0.3 | 0.35 | 0.1 | 0.1 | 1.5 | R |
| 124 | 1 | 1 | 0.15 | 0.3 | 0.35 | 0.1 | 0.1 | 1.0 | R |
| 156 | 10 | 1 | 0.15 | 0.3 | 0.35 | 0.1 | 0.1 | 5.4 | NR |
| 156 | 10 | 1 | 0.15 | 0.3 | 0.35 | 0.1 | 0.1 | 2.4 | R |
| 156 | 10 | 1 | 0.15 | 0.3 | 0.35 | 0.1 | 0.1 | 1.9 | R |
| 158 | 10 | 1 | 0.15 | 0.3 | 0.35 | 0.1 | 0.1 | 3.1 | NR |

The results presented in table B show that patients which combine (i) low or no detectable TNFalpha, (ii) detectable anti-TNF levels, and (iii) essentially low or no ADA level do respond to the treatment. Using the above scoring and weighting factors, patients with a score below 3 can be classified as responders. The results are summarized in the following table.

| Monitoring Score | Patient Status | |
|---|---|---|
| <3 | Responders | Continue treatment (treatment parameters may be adjusted). Primary non-responder patients may be identified and switched to another, non anti-TNF, treatment*. |
| 3-5 | Potential Escapers | Patients should be monitored carefully. Treatment may be continued but possible switch should be considered. |
| >5 | Non-Responders | Switch to another anti-TNF treatment. |

*see patients 24, 32, 40 and 80. For such primary non-responders, it is speculated that TNF plays a minor pathogenic role in disease activity.

Our results show that responders and non responders can be discriminated. Our results further show that the progression from a responder to a non-responder status of a patient can be anticipated, thereby allowing implementation of a substantially improved treatment regimen.

The invention claimed is:

1. A method for immunodetecting an Anti-Drug Antibody (ADA) in a sample from a patient treated with a drug, wherein the drug is a therapeutic antibody or etanercept, said therapeutic antibody or etanercept being directed against a target antigen, the method comprising:

a) verifying the presence of the target antigen in the sample;

b) if present, treating the sample with acid to neutralize the target antigen in the sample, capture of said target antigen by an affinity reagent or immuno-neutralization of said target antigen; and c) immuno-detecting the presence or amount of said ADA in said sample.

2. The method of claim 1, wherein said target antigen is TNFα.

3. The method of claim 1, wherein the therapeutic antibody is an anti-TNFα antibody selected from infliximab, adalimumab, golimumab or certolizumab pegol.

4. The method of claim 1, wherein the sample is a body fluid sample, a blood serum sample or plasma sample.

5. The method according to claim 1, wherein said target antigen, when present, is neutralized by contacting said sample with antibodies that neutralize the activity of said target antigen.

6. The method according to claim 1, wherein said target antigen, when present, is neutralized by treating said sample with an acid to reduce the pH of said sample to below 4 and neutralizing said acid with a base in an amount that raises the pH of the sample to between 5 and 9.

7. The method according to claim 1, wherein said target antigen, when present, is captured by contacting said sample with an affinity reagent comprising a binding reagent specific for said target antigen.

8. The method according to claim 1, wherein said patient is treated with etanercept and said target antigen is TNFα.

9. The method of claim 1, wherein said target antigen is TNFα and said therapeutic antibody is infliximab, adalimumab, golimumab or certolizumab pegol.

* * * * *

UNITED STATES PATENT AND TRADEMARK OFFICE
CERTIFICATE OF CORRECTION

PATENT NO. : 9,063,151 B2  Page 1 of 1
APPLICATION NO. : 13/642874
DATED : June 23, 2015
INVENTOR(S) : Ermis Parussini and Guillaume Noguier It is certified that error appears in the above-identified patent and that said Letters Patent is hereby corrected as shown below:

In the specification,

Column 8,
Line 28, "TNFαc," should read --TNFα,--.

Column 31,
Patient 158, Column "VS", "25" should read --26--.

Signed and Sealed this
First Day of March, 2016

Michelle K. Lee
*Director of the United States Patent and Trademark Office*